United States Patent
Rosati et al.

(10) Patent No.: US 9,399,083 B2
(45) Date of Patent: Jul. 26, 2016

(54) ABSORBENT CORE FOR USE IN ABSORENT ARTICLES

(71) Applicant: The Procter & Gamble Company, Cincinnati, OH (US)

(72) Inventors: Rodrigo Rosati, Frankfurt (DE); Holger Beruda, Schwalbach (DE); Hans Adolf Jackels, Mechernich, DE (US); Juliane Kampus, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 218 days.

(21) Appl. No.: 13/913,997

(22) Filed: Jun. 10, 2013

(65) Prior Publication Data

US 2013/0331806 A1   Dec. 12, 2013

(30) Foreign Application Priority Data

Jun. 8, 2012 (EP) .................................... 12171344

(51) Int. Cl.
*A61F 13/15* (2006.01)
*A61L 15/58* (2006.01)
(Continued)

(52) U.S. Cl.
CPC ................. *A61L 15/58* (2013.01); *A61F 13/53* (2013.01); *A61F 13/534* (2013.01); *A61F 13/535* (2013.01); *A61F 13/536* (2013.01); *A61F 13/537* (2013.01); *A61F 13/539* (2013.01); *A61F 13/5323* (2013.01); *A61F 13/53743* (2013.01); *A61L 15/22* (2013.01); *A61F 13/532* (2013.01); *A61F 13/533* (2013.01);
(Continued)

(58) Field of Classification Search
CPC . A61F 13/539; A61F 13/5323; A61F 13/533; A61F 13/535; A61F 13/536; A61F 13/532; A61F 2013/530481; A61F 2013/53051

USPC ......... 604/367, 366, 370, 372, 374, 375, 377, 604/373, 378, 380

See application file for complete search history.

(56) References Cited

U.S. PATENT DOCUMENTS 3,848,594 A    11/1974 Buell
3,911,173 A    10/1975 Sprague
(Continued)

FOREIGN PATENT DOCUMENTS

DE    10 204 937 A1    8/2003
EP    0 149 880 A2    7/1985
(Continued)

OTHER PUBLICATIONS

EP International Search Report, dated Nov. 27, 2012 (4 pages.

*Primary Examiner* — Jacqueline Stephens
(74) *Attorney, Agent, or Firm* — Wednesday G. Shipp

(57) ABSTRACT

An absorbent core suitable for use in an absorbent article comprising:
  a first absorbent layer, the first absorbent layer comprising a first substrate, and a layer of cross-linked cellulose fibers deposited on said first substrate,
  a second absorbent layer, the second absorbent layer comprising a second substrate, a layer of superabsorbent polymer particles deposited on said second substrate and a fibrous layer of thermoplastic adhesive material covering the layer of superabsorbent polymer particles.
The first and second absorbent layers being combined together such that at least a portion of said fibrous layer of thermoplastic adhesive material contacts at least a portion of the layer of cross-linked cellulose fibers of said first absorbent layer.

20 Claims, 15 Drawing Sheets

(51) Int. Cl.

| | |
|---|---|
| *A61F 13/534* | (2006.01) |
| *A61F 13/535* | (2006.01) |
| *A61F 13/537* | (2006.01) |
| *A61F 13/539* | (2006.01) |
| *A61L 15/22* | (2006.01) |
| *A61F 13/536* | (2006.01) |
| *A61F 13/533* | (2006.01) |
| *A61F 13/532* | (2006.01) |
| *A61F 13/53* | (2006.01) |

(52) U.S. Cl.
CPC .............. *A61F2013/53062* (2013.01); *A61F 2013/530481* (2013.01); *A61F 2013/530554* (2013.01)

(56) References Cited

U.S. PATENT DOCUMENTS

| | | | |
|---|---|---|---|
| 3,929,135 A | 12/1975 | Thompson | |
| 4,324,246 A | 4/1982 | Mullane et al. | |
| 4,342,314 A | 8/1982 | Radel et al. | |
| 4,349,706 A | 9/1982 | Thompson | |
| 4,463,045 A | 7/1984 | Ahr et al. | |
| 4,507,438 A | 3/1985 | Obayashi et al. | |
| 4,515,595 A | 5/1985 | Kievit et al. | |
| 4,541,871 A | 9/1985 | Obayashi et al. | |
| 4,573,986 A | 3/1986 | Minetola et al. | |
| 4,609,518 A | 9/1986 | Curro et al. | |
| 4,629,643 A | 12/1986 | Curro et al. | |
| 4,681,793 A | 7/1987 | Linman et al. | |
| 4,692,578 A | 9/1987 | Wallace | |
| 4,699,622 A | 10/1987 | Toussant et al. | |
| 4,710,189 A | 12/1987 | Lash | |
| 4,731,066 A | 3/1988 | Korpman | |
| 4,785,996 A | 11/1988 | Ziecker et al. | |
| 4,808,178 A | 2/1989 | Aziz et al. | |
| 4,662,875 B1 | 4/1989 | Hirotsu | |
| 4,846,815 A | 7/1989 | Scripps | |
| 4,894,060 A | 1/1990 | Nestegard | |
| 4,909,803 A | 3/1990 | Aziz et al. | |
| 3,860,003 B2 | 6/1990 | Buell | |
| 4,946,527 A | 8/1990 | Battrell | |
| 4,963,140 A | 10/1990 | Robertson et al. | |
| 5,006,394 A | 4/1991 | Baird | |
| 5,137,537 A | 8/1992 | Herron et al. | |
| 5,151,092 A | 9/1992 | Buell et al. | |
| 4,842,666 B1 | 10/1992 | Werenica | |
| 5,221,274 A | 6/1993 | Buell et al. | |
| 5,242,436 A | 9/1993 | Weil et al. | |
| 5,281,683 A | 1/1994 | Yano et al. | |
| 5,331,059 A | 7/1994 | Engelhardt et al. | |
| 5,409,771 A | 4/1995 | Dahmen et al. | |
| 5,499,978 A | 3/1996 | Buell et al. | |
| 5,507,736 A | 4/1996 | Clear et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,574,121 A | 11/1996 | Irie et al. | |
| 5,580,411 A | 12/1996 | Nease et al. | |
| 5,591,152 A | 1/1997 | Buell et al. | |
| 5,607,760 A | 3/1997 | Roe | |
| 5,609,587 A | 3/1997 | Roe | |
| 5,643,588 A | 7/1997 | Roe et al. | |
| H1732 H | 6/1998 | Johnson | |
| 5,837,789 A | 11/1998 | Stockhausen et al. | |
| 5,849,816 A | 12/1998 | Suskind et al. | |
| 5,865,823 A | 2/1999 | Curro | |
| 5,938,648 A | 8/1999 | Lavon et al. | |
| 5,968,025 A | 10/1999 | Roe et al. | |
| 6,004,306 A | 12/1999 | Robles et al. | |
| 6,121,509 A | 9/2000 | Ashraf et al. | |
| 6,143,821 A | 11/2000 | Houben | |
| 4,795,454 C1 | 6/2001 | Dragoo et al. | |
| 6,265,488 B1 | 7/2001 | Fujino et al. | |
| 6,414,216 B1 | 7/2002 | Malowaniec et al. | |
| 6,432,098 B1 | 8/2002 | Kline et al. | |
| 6,472,478 B1 | 10/2002 | Funk et al. | |
| 6,503,979 B1 | 1/2003 | Funk et al. | |
| 6,559,239 B1 | 5/2003 | Riegel et al. | |
| 6,630,611 B1 | 10/2003 | Malowaniec et al. | |
| 6,645,569 B2 | 11/2003 | Cramer et al. | |
| 6,657,015 B1 | 12/2003 | Riegel et al. | |
| 6,716,441 B1 | 4/2004 | Osborne et al. | |
| 6,809,158 B2 | 10/2004 | Ikeuchi et al. | |
| 6,863,933 B2 | 3/2005 | Cramer et al. | |
| 6,979,564 B2 | 12/2005 | Glucksmann et al. | |
| 7,112,621 B2 | 9/2006 | Rohrbaugh et al. | |
| 7,183,360 B2 | 2/2007 | Daniel et al. | |
| 7,199,211 B2 | 4/2007 | Popp et al. | |
| 7,250,481 B2 | 7/2007 | Jaworek et al. | |
| 7,537,832 B2 | 5/2009 | Carlucci et al. | |
| 7,653,111 B2 | 1/2010 | Albrecht et al. | |
| 7,687,596 B2 | 3/2010 | Hermeling et al. | |
| 7,744,576 B2 | 6/2010 | Busam et al. | |
| 7,744,713 B2 | 6/2010 | Blessing et al. | |
| 7,772,420 B2 | 8/2010 | Hermeling et al. | |
| 7,786,341 B2 | 8/2010 | Schneider et al. | |
| 7,838,722 B2 | 11/2010 | Blessing et al. | |
| 8,124,229 B2 | 2/2012 | Stueven et al. | |
| 8,202,957 B2 | 6/2012 | Stueven et al. | |
| 8,205,066 B2 | 6/2012 | Brewer et al. | |
| 8,206,533 B2 | 6/2012 | Hundorf et al. | |
| 8,236,715 B2 | 8/2012 | Schmidt et al. | |
| 8,287,999 B2 | 10/2012 | Schmidt et al. | |
| 2003/0105190 A1 | 6/2003 | Diehl et al. | |
| 2003/0148684 A1 | 8/2003 | Cramer et al. | |
| 2005/0008839 A1 | 1/2005 | Cramer et al. | |
| 2005/0101929 A1 | 5/2005 | Waksmundzki et al. | |
| 2005/0165208 A1 | 7/2005 | Popp et al. | |
| 2007/0093767 A1 | 4/2007 | Carlucci et al. | |
| 2007/0118087 A1 | 5/2007 | Flohr et al. | |
| 2008/0312617 A1 | 12/2008 | Hundorf et al. | |
| 2008/0312621 A1 | 12/2008 | Hundorf et al. | |
| 2008/0312622 A1 | 12/2008 | Hundorf et al. | |
| 2009/0192035 A1 | 7/2009 | Stueven et al. | |
| 2009/0318884 A1 | 12/2009 | Meyer et al. | |
| 2011/0250413 A1 | 10/2011 | Lu et al. | |
| 2011/0268932 A1 | 11/2011 | Catalan et al. | |
| 2011/0319848 A1 | 12/2011 | McKiernqan et al. | |

FOREIGN PATENT DOCUMENTS

| | | |
|---|---|---|
| EP | 0 530 438 A1 | 3/1993 |
| EP | 0 599 476 A1 | 6/1994 |
| WO | WO 90/15830 A1 | 12/1990 |
| WO | WO 93/15702 A1 | 8/1993 |
| WO | WO 93/21237 A1 | 10/1993 |
| WO | WO 95/16746 A1 | 6/1995 |
| WO | WO 95/34329 A1 | 12/1995 |
| WO | WO 99/34841 A1 | 7/1999 |
| WO | WO 2007/047598 A1 | 4/2007 |
| WO | WO 2009/155265 A2 | 12/2009 |

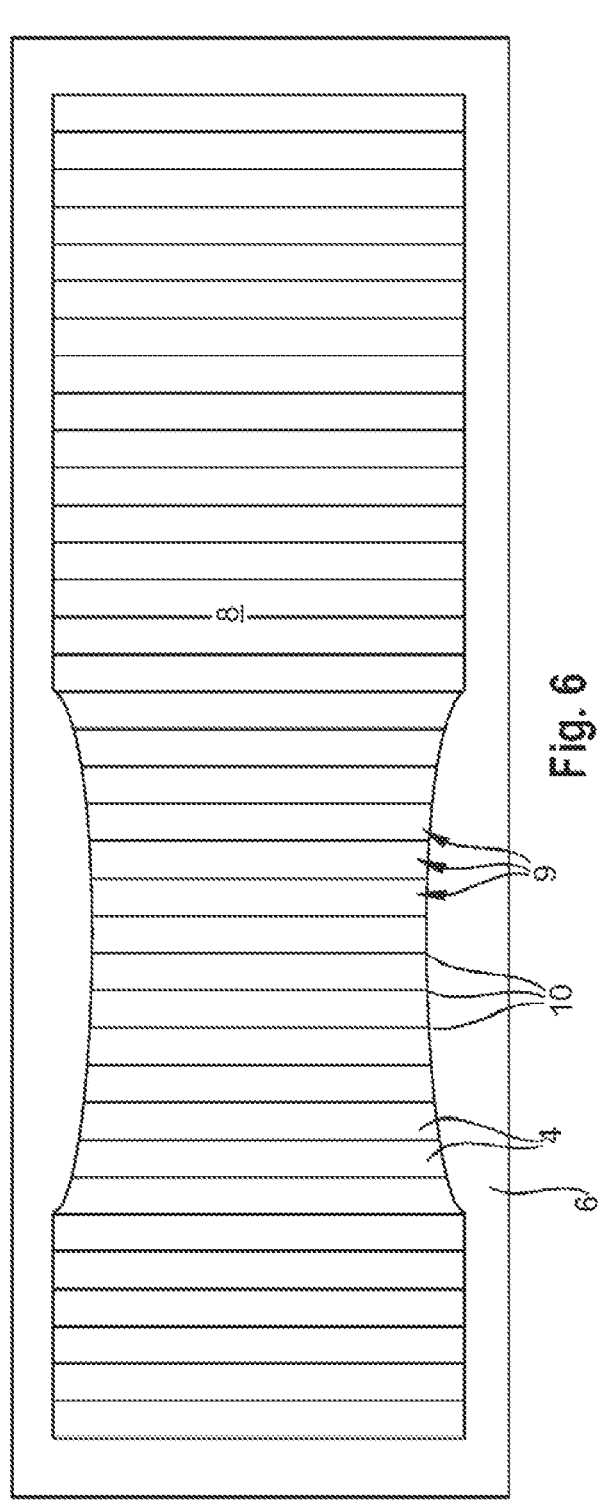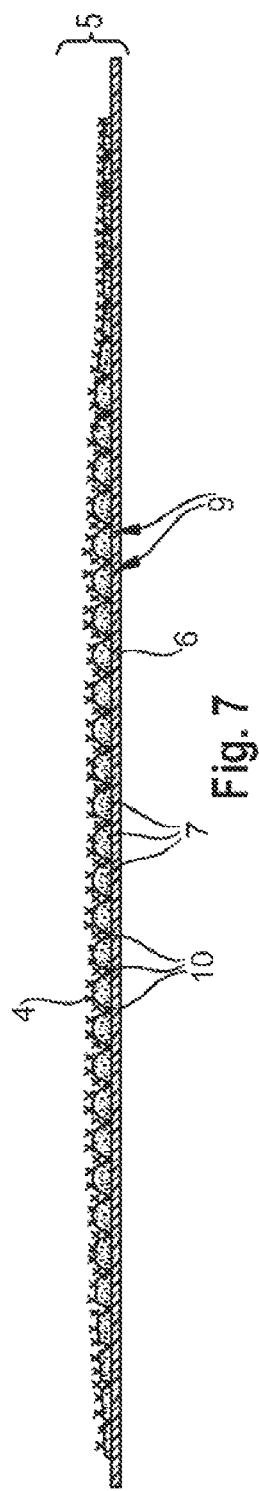

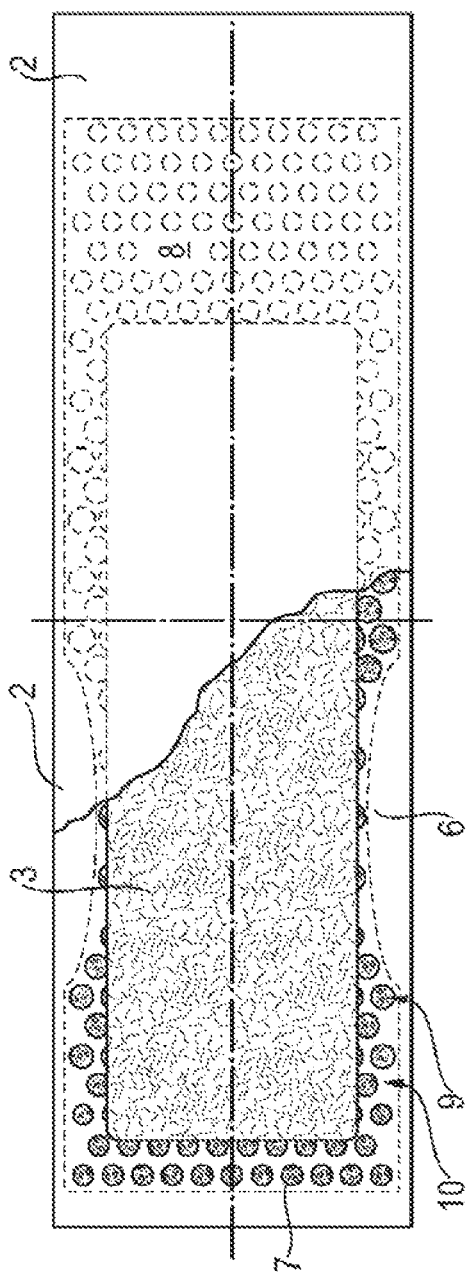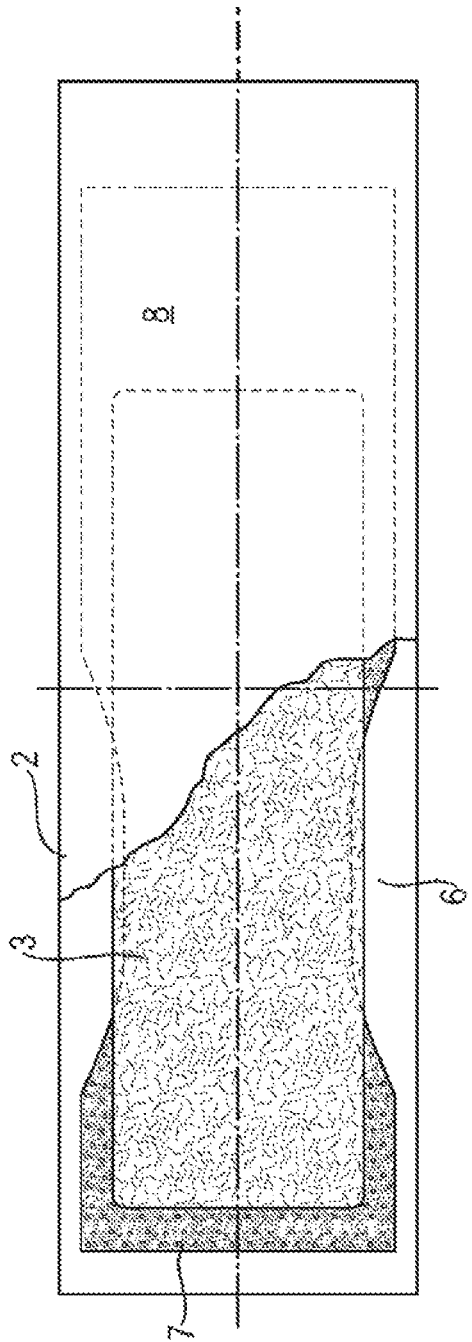

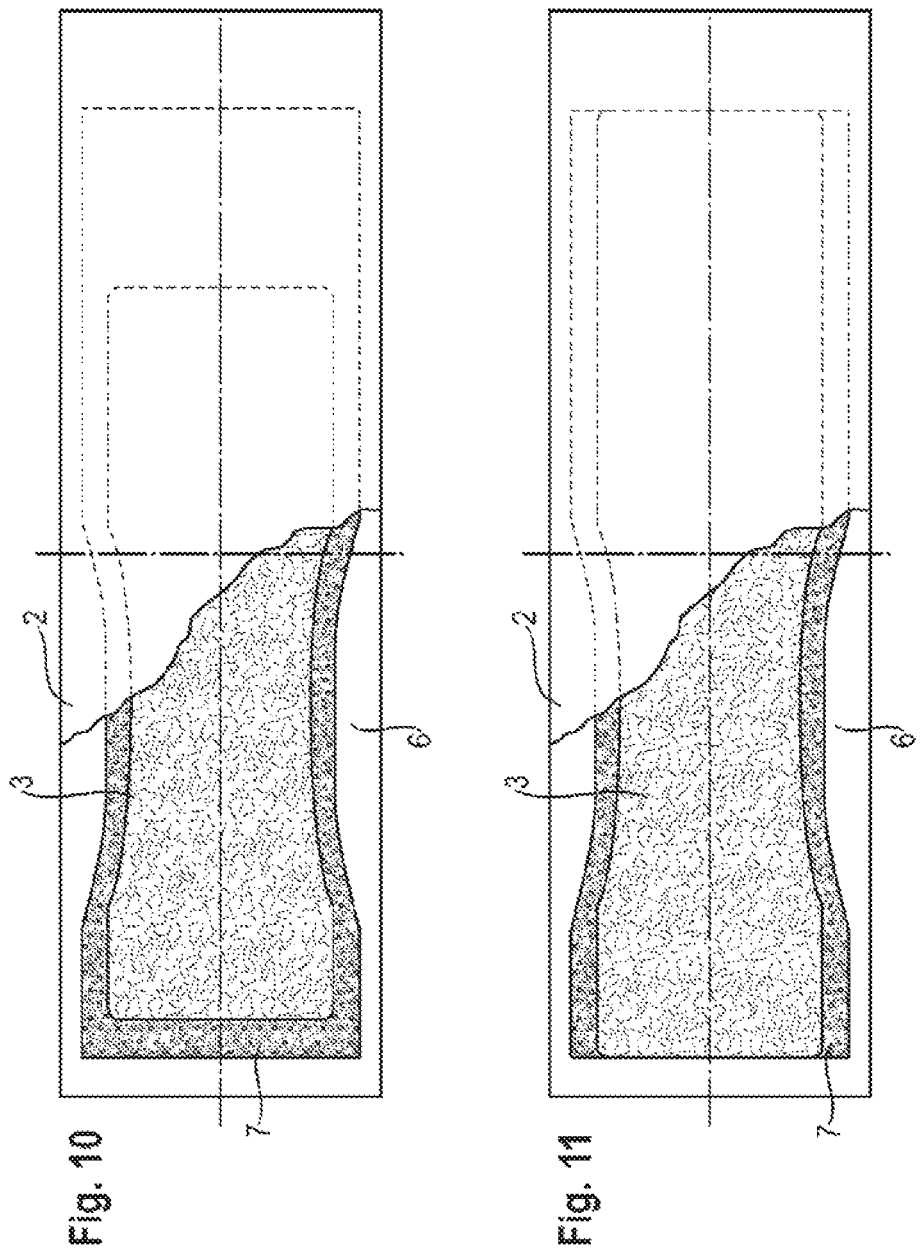

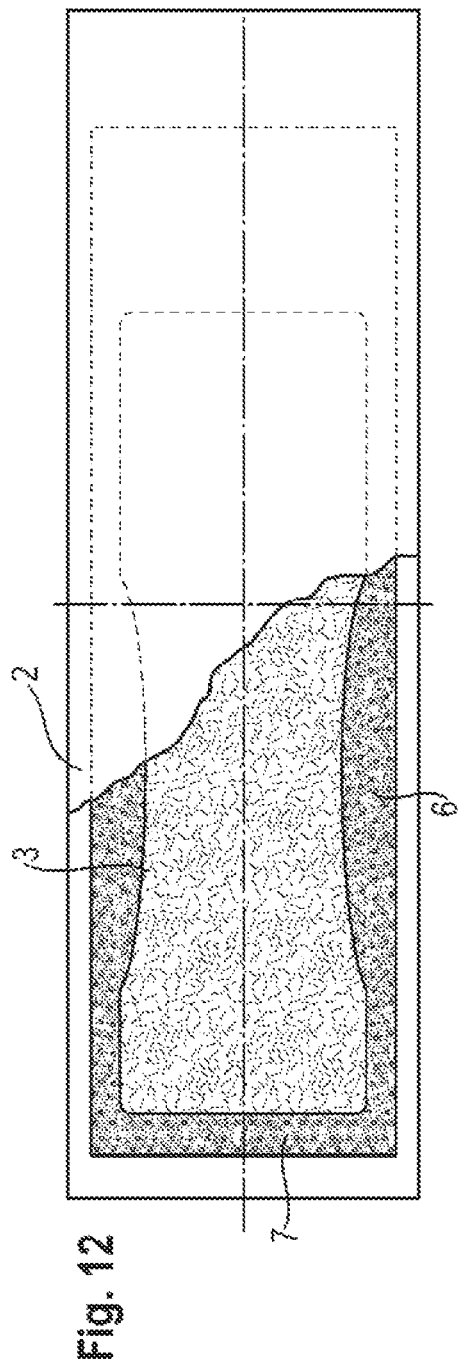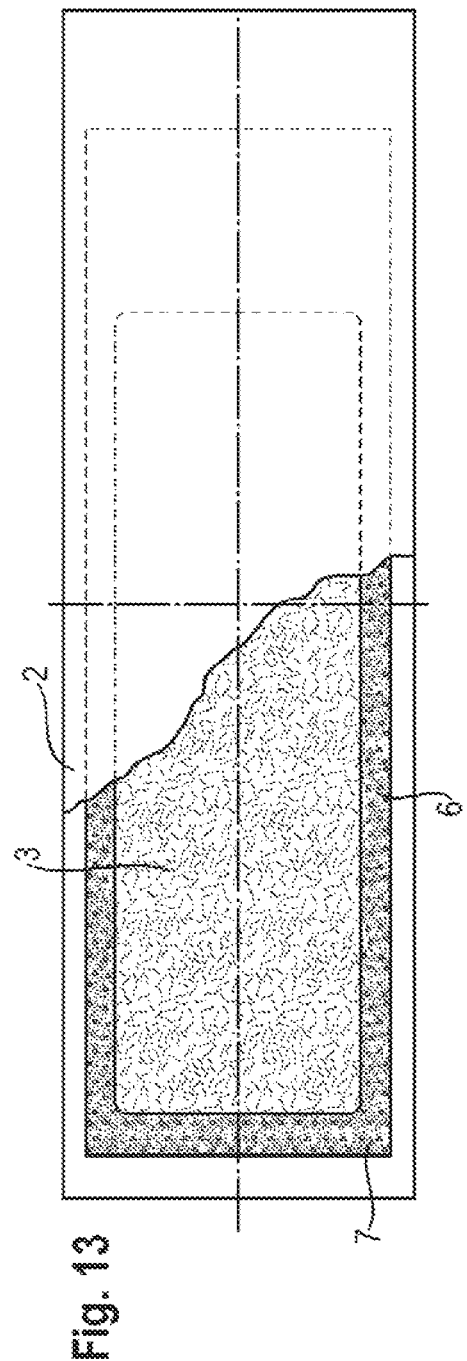

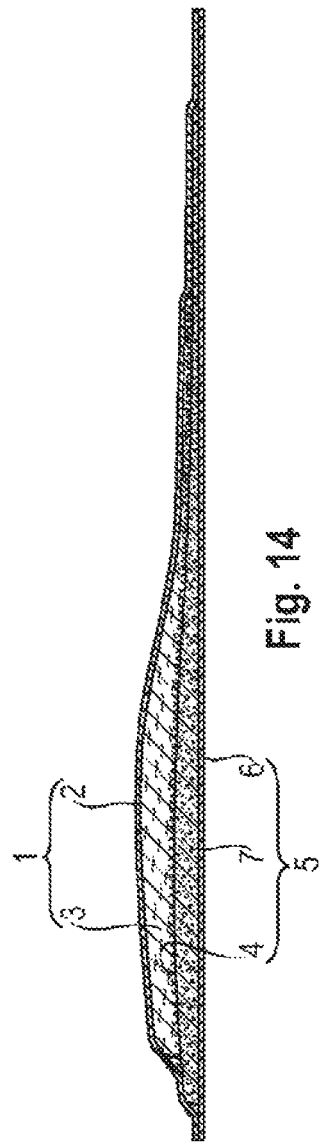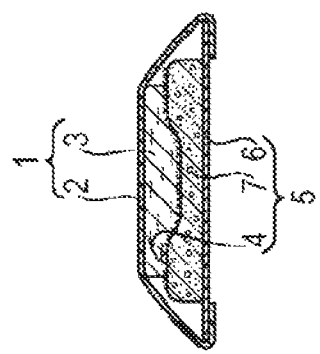

ABSORBENT CORE FOR USE IN ABSORENT ARTICLES

FIELD OF THE INVENTION

The present invention is directed to a new absorbent core suitable for use in absorbent articles, and absorbent articles such as diapers or feminine protection articles comprising such an absorbent core.

BACKGROUND OF THE INVENTION

Absorbent articles for personal hygiene such as disposable diapers, feminine protection pads and adult incontinence undergarments, are designed to absorb and contain body exudates, in particular but not limited to urine. These absorbent articles usually comprise several layers having different functions, for example a topsheet, a backsheet and in-between an absorbent core, among other layers. The absorbent core's function is to absorb and retain the exudates for a prolonged amount of time, for example overnight for a diaper, minimize re-wet to keep the wearer dry and avoid soiling of clothes or bed sheets.

Absorbent cores can expand several times their initial volumes when wet. It is desirable that the cores in this expanded state maintain their structural integrity and do not break or burst even when submitted to a shock such as a child sitting heavily on his diaper. It is also desirable that absorbent cores should be thin (at least when dry) and require as little material as possible for costs and environmental reasons.

The majority of currently marketed absorbent cores for diapers however comprise as absorbent material a blend of comminuted wood pulp with superabsorbent polymer particles (SAP), also called absorbent gelling materials (AGM), see for example U.S. Pat. No. 5,151,092 (Buell). Absorbent articles having a core consisting of essentially SAP as absorbent material (so called "airfelt-free" cores) have also been proposed but are less common than traditional mixed cores (see e.g. WO2008/155699, Hundorf).

US2008/0312621 and US2008/0312622 (Hundorf) describe a disposable absorbent article comprising a chassis including a topsheet and a backsheet, a substantially cellulose free absorbent core located between the topsheet and the backsheet and having a wearer facing side oriented toward a wearer when the article is being worn and an opposed garment facing side, and a liquid acquisition system comprising chemically cross-linked cellulosic fibers disposed between the liquid permeable topsheet and the wearer facing side of the absorbent core. The liquid acquisition system may comprise a nonwoven as an upper acquisition layer and a lower acquisition layer which may comprise chemically cross-linked cellulose fibers. In such a design the lower acquisition layer contacts the upper substrate of the cellulose free absorbent core. A typical process to make such a liquid acquisition system is airlaying the unbound chemically cross-linked cellulose fibers onto the upper acquisition layer nonwoven: in this case, the upper acquisition layer nonwoven always fully covers the lower acquisition layer comprising the chemically cross-linked cellulose fibers.

However it may be desirable to use an upper acquisition layer nonwoven which is shorter or narrower or in an offset position relative to the lower acquisition layer, for instance for cost savings or performance optimization. Additionally if an apertured topsheet is used, it is desired to limit the amount of unbound fibers that could reach the wearer skin through the apertures of the apertured topsheet. Finally the lower acquisition layer may tend to retain liquid due to the hydrophilicity and the pore size of the chemically cross-linked cellulose fibers, whereas the presence of a core cover between the lower acquisition layer and the superabsorbent particles may make it more difficult for the superabsorbent polymers to dewater the lower acquisition layer.

The present inventors have now found a new core structure for absorbent articles, which may address the above described limitations, while delivering a very good fluid handling performance.

SUMMARY OF THE INVENTION

The present invention is directed in first aspect to an absorbent core and in a further aspect to an absorbent article comprising this absorbent core as indicated in the claims. The absorbent core comprises:
  a first absorbent layer (1), the first absorbent layer comprising a first substrate (2), and a layer of cross-linked cellulose fibers (3) deposited on said first substrate, and
  a second absorbent layer (5) comprising a second substrate (6), a layer of superabsorbent polymer particles (7) deposited on said second substrate and a fibrous layer of thermoplastic adhesive material (4) covering the layer of superabsorbent polymer particles (7).

The first and second absorbent layers (1, 5) are combined together such that at least a portion of said fibrous layer of thermoplastic adhesive material (4) contacts at least a portion of the layer of cross-linked cellulose fibers of said second absorbent layer (6).

BRIEF DESCRIPTION OF THE DRAWINGS

FIGS. 5, 6 and 7 shows a perspective, top and cross-section view along the longitudinal axis of an embodiment of a second absorbent layer taken in isolation, where the SAP are applied in bars on the second substrate;

FIG. 8 is a top view of an alternative absorbent core with the SAP applied as dots;

FIG. 9 shows an alternative absorbent core with the SAP layer having a non-rectangular deposition area and the cross-linked cellulose layer having rectangular deposition area;

FIG. 10 shows an alternative absorbent core with the SAP layer and the cross-linked cellulose layer both having a non-rectangular deposition area;

FIG. 11 shows an alternative absorbent core with the deposition area of the cross-linked cellulose layer being longer than in FIG. 10;

FIG. 12 shows a top view of an absorbent core where the cross-linked cellulose layer is shaped (non-rectangular);

FIG. 13 shows a top view of an absorbent core where the deposition areas of both absorbent layers are rectangular;

FIG. 14 shows a schematic cross-section of an absorbent core of the invention in the longitudinal direction of a core according to the invention where both absorbent layers are profiled in the longitudinal direction;

FIG. 15 shows a schematic cross-section of an absorbent core of the invention in the transversal direction where the layer of superabsorbent polymer particles and the crosslinked cellulosic fiber layers are profiled in the transversal direction;

DETAILED DESCRIPTION OF THE INVENTION

Definitions

Figure 1:
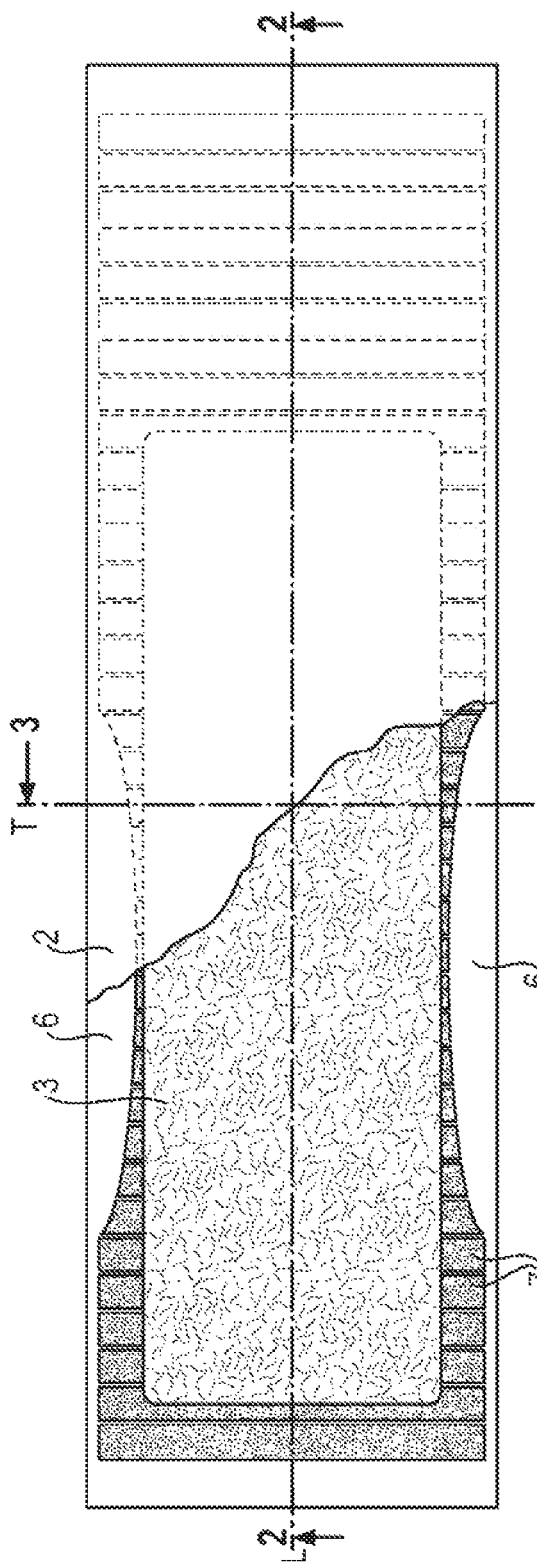
FIG. 1 is a top view of an absorbent core of the invention with the layer of cross-linked cellulose fibers placed above the SAP layer, with some layers partially removed.
Figure 2:
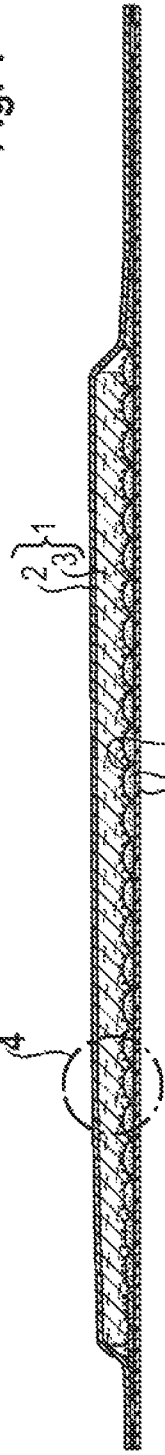
FIG. 2 is a cross-section view of the absorbent core of FIG. 1 along its longitudinal axis L.

The present invention relates to an absorbent core suitable for use in a personal hygiene absorbent article. As used herein, the term "absorbent article" refers to devices which are placed against or in proximity to the body of the wearer to absorb and contain the various exudates discharged from the body such as infant or adult diapers, feminine hygiene articles and the like. Typically these articles comprise a topsheet, backsheet, optionally an acquisition system (which may be comprised of one or several layers) and possibly other components, with the absorbent core normally placed between the backsheet and the acquisition system or topsheet. The absorbent core is typically the component of the article having the most absorbent capacity.

As used herein, the term "absorbent core" refers to an independent component suitable for use in an absorbent article comprising absorbent materials as defined in the claims and enclosed between a first substrate and a second substrate. The term "absorbent core" as used herein does not include the topsheet, the backsheet and (if present) an acquisition system which is not integral part of the absorbent core, in particular which is not placed between the first substrate and the second substrate.

A "nonwoven web" as used herein means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m$^2$).

"Comprise," "comprising," and "comprises" are open ended terms, each specifies the presence of what follows, e.g., a component, but does not preclude the presence of other features, e.g., elements, steps, components known in the art, or disclosed herein. Any preferred or exemplary embodiments described below are not limiting the scope of the claims, unless specifically indicated to do so.

First and Second Substrates 2, 6

The first and second substrates 2, 6 may be formed by any materials suitable for receiving the absorbent materials deposited thereon. Typical substrate materials used in the production of conventional cores may be used, in particular paper, tissues, films, wovens or nonwovens, or laminate of any of these. The first and second substrates may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1 or US2011/0250413A1. Nonwoven materials provided from synthetic fibers may be used, such as PE, PET and in particular PP.

The first substrate 2 and second substrate 6 may be made of the same type of material, or may be made of different materials or one of the substrate may be treated differently than the other to provide it with different properties. As the polymers used for nonwoven production are inherently hydrophobic, they are preferably coated with hydrophilic coatings if placed on the fluid receiving side of the absorbent core. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g. as described in WO 02/064877.

Permanently hydrophilic nonwovens are also useful in some embodiments. Surface tension, as described in U.S. Pat. No. 7,744,576 (Busam et al.), can be used to measure how permanently a certain hydrophilicity level is achieved. Liquid strike through, as described in U.S. Pat. No. 7,744,576, can be used to measure the hydrophilicity level. The first and/or second substrate may in particular have a surface tension of at least 55, preferably at least 60 and most preferably at least 65 mN/m or higher when being with saline solution. The substrate may also have a liquid strike through time of less than 5 s for a fifth gush of liquid. These values can be measured using the test methods described in U.S. Pat. No. 7,744,576B2: "Determination Of Surface Tension" and "Determination of Strike Through" respectively.

Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A substrate having a lower contact angle between the water and the surface of substrate may be said to be more hydrophilic than another.

The substrates may also be air-permeable. Films useful herein may therefore comprise micro-pores. The first and second substrate may have for example an air-permeability of from 40 or from 50, to 300 or to 200 m$^3$/(m$^2$×min), as determined by EDANA method 140-1-99 (125 Pa, 38.3 cm$^2$). The first and/or second substrate may alternatively have a lower air-permeability, e.g. being non-air-permeable, for example to facilitate handling on a moving surface comprising vacuum.

Figure 3:
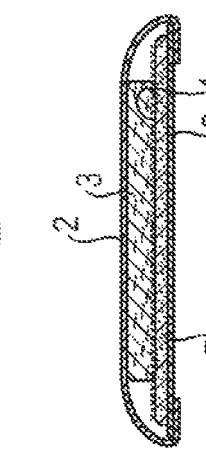
FIG. 3 is a cross-section view of the absorbent core of FIG. 1 along its transversal axis T.

As shown in FIG. 3 for example, the first substrate 2 may be placed on one side of the core (the top side as represented therein) and extends around the core's longitudinal edges to partially wrap the opposed (bottom) side of the core. The second substrate 6 can be positioned between the wrapped flaps of the first substrate 2 and the rest of the core. The flaps of the first substrate 2 and the second substrate 6 may be glued. This so called C-wrap construction can provide benefits such as improved resistance to bursting in a wet loaded state. The transversal edges of the core may then also be sealed for example by gluing to provide complete encapsulation of the absorbent materials of the core across the whole of the periphery of the core. As an alternate construction, in the so-called sandwich construction, the first and second substrates may extend outwardly and be sealed along the whole or parts of the periphery of the core, for example along the longitudinal edges of the core, typically by gluing and/or heat/pressure bonding.

Typically neither first nor second substrates need to be shaped, so that they can be rectangularly cut for ease of production but of course other shapes are possible.

First Absorbent Layer 1

The first absorbent layer 1 comprises the first substrate 2 as indicated above, and a layer of cross-linked cellulose fibers 3 deposited on said first substrate, in particular chemically cross-linked cellulosic fibers. This type of material has been used in the past in disposable diapers as part of an acquisition system placed outside the core, see for example US 2008/0312622 A1 (Hundorf). However it has not been suggested to use it directly inside an absorbent core. The cross-linked cellulosic fibers may be crimped, twisted, or curled, or a combination thereof including crimped, twisted, and curled. The layer of crosslinked cellulose fibers may have a water retention value of from 25 to 60, preferably from 30 to 45, measured as indicated in the procedure disclosed in U.S. Pat. No. 5,137,537.

Exemplary chemically cross-linked cellulosic fibers are disclosed in U.S. Pat. No. 5,549,791, U.S. Pat. No. 5,137,537, WO9534329 or US2007/118087. Exemplary cross-linking agents include polycarboxylic acids such as citric acid and/or polyacrylic acids such as acrylic acid and maleic acid copolymers.

For example, the crosslinked cellulosic fibers may have between about 0.5 mole %, and about 10.0 mole % of a C2-C9 polycarboxylic acid cross-linking agent, calculated on a cellulose anhydroglucose molar basis, reacted with said fibers in an intrafiber ester crosslink bond form. The C2-C9 polycarboxylic acid cross-linking agent may be selected from the group consisting of:

aliphatic and alicyclic C2-C9 polycarboxylic acids having at least three carboxyl groups per molecule; and
aliphatic and alicyclic C2-C9 polycarboxylic acids having two carboxyl groups per molecule and having a carbon-carbon double bond located alpha, beta to one or both of the carboxyl groups, wherein one carboxyl group in said C2-C9 polycarboxylic acid crosslinking agent is separated from a second carboxyl group by either two or three carbon atoms. The fibers may have in particular between about 1.5 mole % and about 6.0 mole % crosslinking agent, calculated on a cellulose anhydroglucose molar basis, reacted therewith in the form of intrafiber ester crosslink bonds. The cross-linking agent may be selected from the group consisting of citric acid, 1, 2, 3, 4 butane tetracarboxylic acid, and 1, 2, 3 propane tricarboxylic acid, in particular citric acid.

Polyacrylic acid cross-linking agents may also be selected from polyacrylic acid homopolymers, copolymers of acrylic acid, and mixtures thereof. The fibers may have between 1.0 weight %, and 10.0 weight %, preferably between 3 weight % and 7 weight %, of these cross-linking agents, calculated on a dry fiber weight basis, reacted therewith in the form of intrafiber crosslink bonds. The cross-linking agent may be a polyacrylic acid polymer having a molecular weight of from 500 to 40,000, preferably from 1,000 to 20,000. The polymeric polyacrylic acid cross-linking agent may be a copolymer of acrylic acid and maleic acid, in particular wherein the weight ratio of acrylic acid to maleic acid is from 10:1 to 1:1, preferably from 5:1 to 1.5:1. An effective amount of citric acid may be further mixed with said polymeric polyacrylic acid cross-linking agent.

The layer of cross-linked cellulose fibers of the invention deposited may comprise other fibers, but this layer comprises at least 50%, advantageously at least 60% or 70% or 80% or 90% or more, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The layer of cross-linked cellulose fibers may typically deposited at a basis weight of from 30 to 400 g/m$^2$, in particular from 100 to 300 g/m$^2$ in its deposition area. The density of this layer may vary depending on the compression of the core, but may be of between 0.03 to 0.15 g/cm$^3$, in particular 0.08 to 0.10 g/cm$^3$ measured at 0.30 psi (2.07 kPa). The absorbent core may typically comprise from 5 to 50 weight percent, preferably from 10 to 35 weight percent, of cross-linked cellulose fibers (including the cross-linking agents but not other fibers) by total weight of the core (first and second layer combined).

The first absorbent layer 1 may also comprise an auxiliary adhesive, which is not illustrated in the figures. The auxiliary adhesive may be applied on the first substrate 2 before deposition of the cross-linked fibers for enhancing their adhesion to the first substrate 2.

The cross-linked cellulosic fibers provide higher resilience and therefore higher resistance to the first absorbent layer against the compression in the product packaging or in use conditions, e.g. under baby weight. This provides the core with a higher void volume, permeability and liquid absorption, and hence reduced leakage and improved dryness.

Second Absorbent Layer 5—SAP Layer 7

The second absorbent layer 5 comprises a layer of superabsorbent polymer particles (SAP) 7 deposited on the second substrate 6 and a fibrous layer of adhesive material 4 covering the layer of superabsorbent polymer particles (7). The SAP useful in the present invention include a variety of water-insoluble, but water-swellable polymers capable of absorbing large quantities of fluids. "Superabsorbent polymers" as used herein refer to absorbent material which are cross-linked polymeric materials that can absorb at least 10 times their weight of an aqueous 0.9% saline solution as measured using the Centrifuge Retention Capacity (CRC) test (EDANA method WSP 241.2-05E). The SAP of the invention may in particular have a CRC value of more than 20 g/g, or more than 24 g/g, or of from 20 to 50 g/g, or from 20 to 40 g/g, or 24 to 30 g/g.

The superabsorbent polymer can be in particulate form so as to be flowable in the dry state. Typical particulate absorbent polymer materials are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in the PCT Patent Application WO07/047,598 or for example WO07/046,052 or for example WO2009/155265 and WO2009/155264. In some embodiments, suitable superabsorbent polymer particles may be obtained by current state of the art production processes as is more particularly as described in WO 2006/083584. The superabsorbent polymers are preferably internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068. WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962 as well as cross-linkers described in WO2009/155265. The superabsorbent polymer particles may be externally surface cross-linked, or: post cross-linked). Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502, bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A 102 04 937, bicyclic amide acetals as described in DE-A 103 34 584, oxetane and cyclic ureas as described in EP-A 1 199 327 and morpholine-2,3-dione and its derivatives as described in WO 03/031482.

In some embodiments, the SAP are formed from polyacrylic acid polymers/polyacrylate polymers, for example having a neutralization degree of from 60% to 90%, or about 75%, having for example sodium counter ions.

The SAP useful for the present invention may be of numerous shapes. The term "particles" refers to granules, fibers, flakes, spheres, powders, platelets and other shapes and forms known to persons skilled in the art of superabsorbent polymer particles. In some embodiments, the superabsorbent polymer particles can be in the shape of fibers, i.e. elongated, acicular superabsorbent polymer particles. In those embodiments, the superabsorbent polymer particles fibers have a minor dimension (i.e. diameter of the fiber) of less than about 1 mm, usually less than about 500 µm, and preferably less than 250 µm down to 50 µm. The length of the fibers is preferably about 3 mm to about 100 mm. The fibers can also be in the form of a long filament that can be woven.

Typically, SAP are spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 µm, or from 50 to 850 µm, preferably from 100 to 500 µm, more preferably from 150 to 300 µm, as measured according to EDANA method WSP 220.2-05. SAP having a relatively low particle size help to increase the surface area of the absorbent material which is in contact with liquid exudates and therefore support fast absorption of liquid exudates.

The SAP may have a particle sizes in the range from 45 µm to 4000 µm, more specifically a particle size distribution within the range of from 45 µm to about 2000 µm, or from about 100 µm to about 1000, 850 or 600 µm. The particle size distribution of a material in particulate form can be determined as it is known in the art, for example by means of dry sieve analysis (EDANA 420.02 "Particle Size distribution).

In some embodiments herein, the superabsorbent material is in the form of particles with a mass medium particle size up to 2 mm, or between 50 microns and 2 mm or to 1 mm, or preferably from 100 or 200 or 300 or 400 or 500 µm, or to 1000 or to 800 or to 700 µm; as can for example be measured by the method set out in for example EP-A-0691133. In some embodiments of the invention, the superabsorbent polymer material is in the form of particles whereof at least 80% by weight are particles of a size between 50 µm and 1200 µm and having a mass median particle size between any of the range combinations above. In addition, or in another embodiment of the invention, said particles are essentially spherical. In yet another or additional embodiment of the invention the superabsorbent polymer material has a relatively narrow range of particle sizes, e.g. with the majority (e.g. at least 80% or preferably at least 90% or even at least 95% by weight) of particles having a particle size between 50 µm and 1000 µm, preferably between 100 µm and 800 µm, and more preferably between 200 µm and 600 µm.

Suitable SAP may for example be obtained from inverse phase suspension polymerizations as described in U.S. Pat. Nos. 4,340,706 and 5,849,816 or from spray- or other gas-phase dispersion polymerizations as described in US Patent Applications No. 2009/0192035, 2009/0258994 and 2010/0068520. In some embodiments, suitable SAP may be obtained by current state of the art production processes as is more particularly described from page 12, line 23 to page 20, line 27 of WO 2006/083584.

The surface of the SAP may be coated, for example, with a cationic polymer. Preferred cationic polymers can include polyamine or polyimine materials. In some embodiments, the SAP may be coated with chitosan materials such as those disclosed in U.S. Pat. No. 7,537,832 B2. In some other embodiments, the SAP may comprise mixed-bed Ion-Exchange absorbent polymers such as those disclosed in WO 99/34841 and WO 99/34842.

The layer of SAP of the invention will typically comprise only one type of SAP, but it is not excluded that a blend of SAPs may be used. It may be preferred to use a relatively high fluid permeable SAP in the layer, especially if the second absorbent layer comprising the layer of SAP is orientated towards the wearer when in use. The fluid permeability of a superabsorbent polymer can be quantified using its Urine Permeability Measurement (UPM) value, as measured in the test disclosed further below.

The UPM of the SAP may for example be of at least $10\times10^{-7}$ cm$^3$·sec/g·m, or at least $30\times10^{-7}$ cm$^3$·sec/g, or at least $50\times10^{-7}$ cm$^3$·sec/g, or more, e.g. at least 80 or $100\times10^{-7}$ cm$^3$·sec/g. The flow characteristics can also be adjusted by varying the quantity and distribution of the SAP used in the second absorbent layer.

The superabsorbent polymer particles 7 are deposited as layer on a deposition area 8 of the second substrate 6 according to a certain deposition pattern. The deposition area 8 can be defined by its periphery. The deposition area 8 of the SAP on the second substrate may typically be smaller than the available surface of the second substrate 6.

The deposition area 8 can take various shapes, in particular display a so-called "dog bone" or "hour-glass" shape, which shows a tapering along its width in the middle or "crotch" region of the core, as exemplarily shown in the embodiment of FIG. 1-5. In this way, the SAP deposition area may have a relatively narrow width in an area of the core intended to be placed in the crotch region of the absorbent article. This may provide for example better wearing comfort. The SAP deposition area 8 may thus have a width (as measured in the transversal direction) at its narrowest point which is less than about 100 mm, 90 mm, 80 mm, 70 mm, 60 mm or even less than about 50 mm. This narrowest width may further be for example at least 5 mm, or at least 10 mm, smaller than the width of the deposition area at its largest point in the front and/or back regions of the deposition area 8. The SAP deposition area 8 can also be generally rectangular, for example as shown in FIGS. 8, 9 and 13, but other deposition areas can also be used such as a "T" or "Y" shape".

The SAP may be uniformly deposited (i.e. with uniform basis weight) within the deposition area 8, but it will be typically advantageous to apply the superabsorbent material non-uniformly within the SAP deposition area in order to form land areas 9 comprising a relatively high amount of SAP and junction areas 10 formed between the land areas with relatively low amount, and preferably substantially free of SAP, such that the SAP are discontinuously distributed on the second substrate. Although the plural form is used, it is not excluded that the deposition area 8 comprises only a single connected land area and/or a single connected junction area, as seen for example in FIG. 8 having a single connected junction area. By "substantially free of SAP" it is meant that no SAP are intentionally deposited in the junction areas, but these may comprise isolated superabsorbent polymer particles involuntarily deposited due to process variability.

The land areas 9 thus can form discrete or disconnected pockets of SAP enclosed on one side by the second substrate 6 and the other by the fibrous layer of adhesive material 4. The junction areas 10 can help the fibrous layer of thermoplastic adhesive material 4 to contact and adhere to the second substrate 6. This can provide a better immobilization of the SAP present in the land areas to the second substrate. In the land areas, the fibrous layer of thermoplastic adhesive material 4 typically does not contact the second substrate directly.

The land areas 9 and junction areas 10 can have a variety of shapes, including but not limited to, transversal and/or longitudinal bars, dots, circles, oval, square, rectangular, triangular, and the like. Within the deposition area 8, the total surface of the land areas 9 will typically be larger than the total surface of the junction areas 10. Within the SAP deposition area 8, the average distance between two neighboring land areas will in general be relatively low, typically below 6 mm, 4 mm, 2 mm or less. As the core is saturated with a fluid, the pockets of SAP formed in the land areas will typically expand into the junction areas so that these will diminish up to a point where neighboring land areas will come into contact with each other. Typically, the junction areas will no longer be visible when the article is saturated with a fluid (e.g. after dipping in a Jayco Synthetic Urine solution as described further below).

In addition to the junction areas 10, the core may also comprise one or more, typically one or more pairs of, channels 11 which are typically much larger regions substantially free of SAP within the deposition area and/or may extend substantially longitudinally. Typically these channels will remain visible after saturation. These will be discussed further below. It is also not excluded that the core comprise several deposition areas spaced apart from another, for example longitudinally or transversally extending areas separated by channels having a relatively larger widths.

Figure 5:
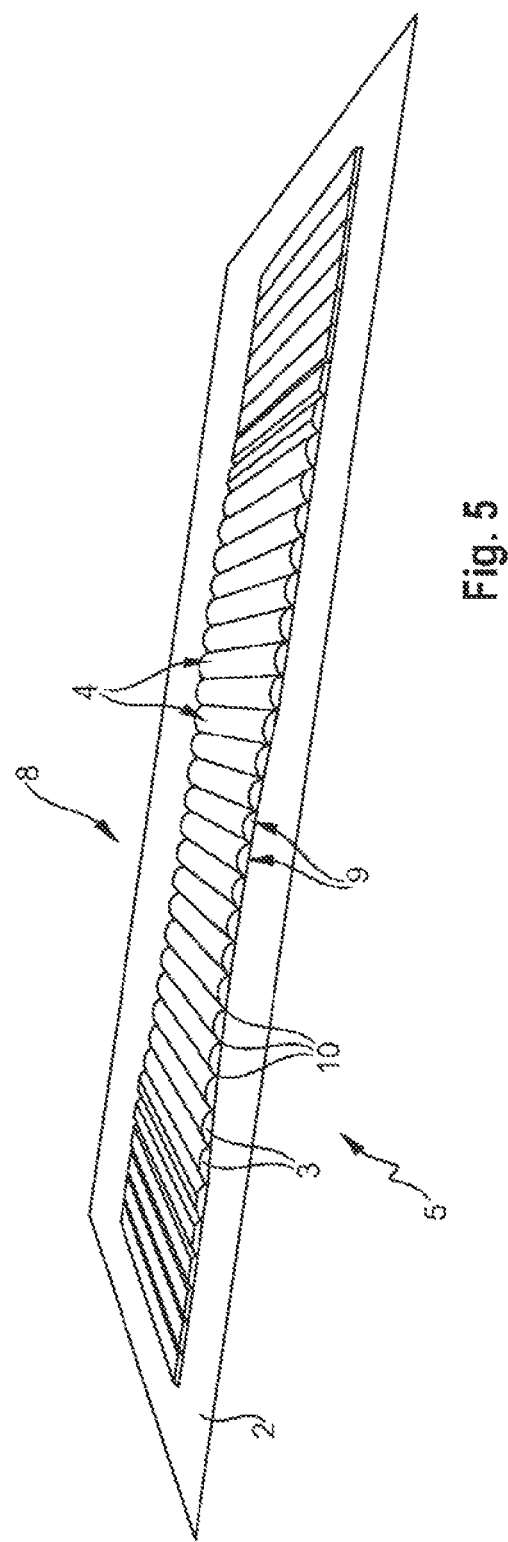

In the SAP deposition area 8, the land areas 9 and the junction areas 10 may form transversally oriented alternating bars, as exemplarily shown in FIG. 1 and in more details in FIG. 5-7. In this case, the land areas 9 may preferably be wider than the junction areas 10 as measured in the longitudinal direction. For example the land areas may have a width comprised between 2 and 40 mm, in particular between 4-20 mm, for example 10 mm, and the junction areas between these bars may have a width between 0.2-5 mm, or 0.5-4 mm, or 1-3 mm. The length of the bars may also vary in the transversal direction. For example it may be advantageous that the bars may be relatively shorter in the central area of the core and relatively longer at the front and/or the back of the core.

The basis weight (amount deposited per unit of surface) of the SAP may also be varied along the deposition area 8 to create a profiled distribution of the SAP in the longitudinal direction (e.g. as shown on FIG. 5), in the transversal direction, or both directions of the core. Hence along the longitudinal axis of the core, the basis weight of the SAP deposited in different land areas may be varied, as well as along the transversal axis, or any axis parallel to any of these axis. When the SAP deposition pattern comprises land areas separated by junction areas, the basis weight of SAP in a land area of relatively high basis weight may thus be for example at least 10%, or 20%, or 30%, or 40%, or 50% higher than in a land area of relatively low basis weight. In particular the land areas present in a deposition area of the core having a narrowed width, or more generally a small surface area, (for example in a middle or intermediate region between the front and back regions of the core) may have on average more SAP per unit of surface deposited as compared to other deposition areas having a larger deposition area.

FIG. 8 shows another type of deposition area 8, wherein a grid pattern of substantially circular land areas 8 is shown, each land area 8 being surrounded by a single connected junction area 9. In general, the land areas may be regularly spaced and sized, but the size and spacing of the land areas may also vary within the deposition area. Each circular land areas may also have different amount of SAP deposited per unit of surface. As shown in the example of FIG. 8 the size of the land areas (dots) may be larger in the central region of the core than in the front and back regions, and the basis weight of SAP in each land area may also vary, e.g. with a higher basis weight in the middle region. The deposition area may comprise a narrower middle region, normally in the region of the core intended to be placed in the crotch area of the user in the finished article.

When the land areas are deposited in a grid pattern, for example of substantially circular land pattern as shown on FIG. 8, the surface of each land area may be comprised between 1 mm$^2$ to 50 mm$^2$ and the distance center to center between two adjacent land areas may be between 2 to 20 mm.

It is also possible to combine different patterns for the land areas, such as bars and dots (circular land areas), for example bars in the center of the core and dots on the front and the back. In fact, in one process of the invention, the SAP are printed sequentially as a continuous series of dots which together form a bar when a relatively high amount of SAP is applied for each dot so that they overlap when printed. When a lower amount of SAP is used for each dot, these dots may become smaller and distinct, so that a bar pattern and dot pattern can be combined on the same deposition area.

From the preceding, it is clear that with the cores of the invention, it is possible to design cores with a great freedom, in particular to best adapt the distribution of the SAP in the area of the core where it will be most needed for the targeted user (e.g. according to the sex or the age of the baby) while keeping the core comfortable to wear.

It has been found that, for most absorbent articles such as diapers, the liquid discharge occurs predominately in the front half of the diaper. The front half of the absorbent core may therefore comprise most of the absorbent capacity of the core. Thus, the front half of the absorbent core may comprise more than about 60% of the SAP, or more than about 65%, 70%, 75% or 80% of the superabsorbent material.

The total amount of SAP present in the absorbent core may also vary according to expected user. Feminine protection articles or diapers for new born may require much less SAP than infant or adult incontinence diapers. For infant diapers the total amount of SAP may be for example comprised from about 1 to 50 g, in particular from 2 to 20 g. The average basis weight within the (or "at least one", if several are present) deposition area of the SAP may be of at least 50, 100, 200, 300, 400, 500 or more g/m$^2$.

The absorbent core may typically comprise from 30 to 90 weight percent, in particular from 50 to 80 weight percent of SAP by total weight of the core. The weight ratio of SAP to cross-linked cellulose fibers (including the cross-linking agent but no fibers which are not cross-linked cellulosic fibers) may typically range from 1:1 to 10:1, in particular from 1.5:1 to 8:1, or from 2:1 to 5:1.

The second absorbent layer may advantageously comprise little or no airfelt (cellulose) fibers mixed with the SAP, in particular the second absorbent layer may be comprise less than 20%, 15%, 10%, 5% airfelt (cellulose) fibers by weight of the second absorbent layer, or even be substantially cellulose free.

The SAP layer may be deposited using known techniques which allow relatively precise deposition of SAP at relatively high speed. In particular the SAP printing technology as disclosed for example in US2006/24433 (Blessing), US2008/0312617 and US2010/0051166A1 (both to Hundorf et al.) may be used. This technique uses a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate.

The second absorbent layer 5 may also comprise an auxiliary adhesive, which is not illustrated in the figures. The auxiliary adhesive may be applied on the second substrate 6 before deposition of the SAP for enhancing adhesion of the SAP 7 and the fibrous thermoplastic adhesive material 4 to second substrate 6. The auxiliary adhesive may comprise the same thermoplastic adhesive material that makes the fibrous layer covering the SAP layer but may also comprise other adhesives including but not limited to standard sprayable hot melt adhesives, such as H. B. Fuller Co. (St. Paul, Minn.) Product No. HL-1620-B, which may be cheaper than the thermoplastic adhesive material applied on the SAP of the second absorbent layer. The auxiliary adhesive may be applied to the second substrate by any suitable means, such as in about 0.5 to about 1 mm wide slots spaced about 0.5 to about 2 mm apart orientated in the Machine Direction of the core making process, typically the longitudinal direction. The second absorbent layer 5 may also optionally include a layer of construction glue to help the first and second absorbent layers adhering to each other, in particular the construction glue may be applied directly on the fibrous layer of thermoplastic adhesive material 4, as is illustrated in the exemplary process described below. U.S. Pat. No. 5,833,678 discloses examples of auxiliary adhesives and construction glues suitable for use in the present invention, as are also well known in the art.

Second Absorbent Layer 5—Fibrous Layer 4

The second absorbent layer 5 further comprises a fibrous layer of thermoplastic adhesive material 4 which covers at least partially and preferably completely the SAP layer 7. Thus this fibrous layer (not shown in FIG. 1 but represented by crosses in FIG. 4) is applied on the surface of the layer formed by the deposited SAP. "Fibrous layer" refers to a network of fibers of thermoplastic adhesive material which are applied in a molten state directly to the surface of the layer formed by the SAP. The SAP directly in contact with the fibers are directly immobilized and the remaining SAP underneath are sandwiched between the second substrate and the fibrous layer. This fibrous layer 4 can preferably immobilize the SAP in both the dry and wet state. Examples of thermoplastic adhesive material can be found for example in US2008/0312621 (Hundorf et al.).

Figure 4:
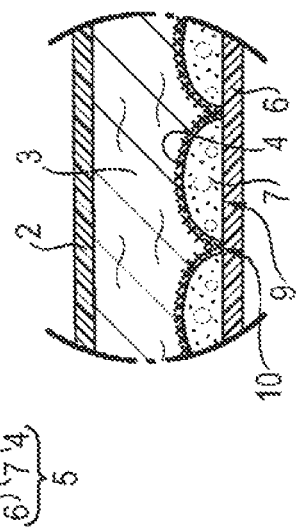
FIG. 4 is a close-up view of part of the cross-section of FIG. 2.

The fibrous adhesive layer 4 may be at least partially in contact with the SAP in the land areas 9 and at least partially in contact with the second substrate layer in the junction areas 10 of the second absorbent layer 5. FIG. 4 shows in more detail such a structure, where the SAP layer 7 is provided as a discontinuous layer, and a layer of fibrous thermoplastic adhesive material 4 covers the layer of SAP, such that the thermoplastic adhesive material 4 is in direct contact with the SAP in land areas 9 but also with the inner surface of the substrate 6 in the junction areas 10. This imparts an essentially three-dimensional structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the SAP in the land area, and thereby immobilizes this material.

In a further aspect, the fibrous layer of thermoplastic adhesive material 4 can bond to the second substrate 6 and thus at least partially affixes the SAP to the second substrate 6. Thus, the fibrous thermoplastic adhesive material 4 can immobilize the SAP when wet, such that the absorbent core achieves an SAP loss of no more than about 70%, 60%, 50%, 40%, 30%, 20%, 10% according to the Wet Immobilization Test described in WO2010/0051166A1. Some thermoplastic adhesive material 4 can also penetrate into both the SAP layer 5 and the second substrate 6, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive material may also provide a very good immobilization of absorbent material 7 when the absorbent core is dry. The thermoplastic adhesive material may also be referred to as a hotmelt adhesive.

It has been found that those thermoplastic adhesive materials which are most useful for immobilizing the SAP combine good cohesion and good adhesion behavior. Good adhesion may promote good contact between the thermoplastic adhesive material and the SAP and the substrate. Good cohesion reduces the likelihood that the adhesive breaks, in particular in response to external forces, and namely in response to strain. When the absorbent core absorbs liquid, the SAP material swells and subjects the thermoplastic adhesive material to external forces. The thermoplastic adhesive material may allow for such swelling, without breaking and without imparting too many compressive forces, which would restrain the absorbent particulate polymer material from swelling.

The thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hotmelt adhesive comprising at least one thermoplastic polymer in combination with other thermoplastic diluents such as tackifying resins, plasticizers and additives such as antioxidants.

The thermoplastic polymer has typically a molecular weight (Mw) of more than 10,000 and a glass transition temperature (Tg) usually below room temperature or −6° C.<Tg<16° C. Typical concentrations of the polymer in a hotmelt are in the range of about 20 to about 40% by weight. The thermoplastic polymers may be water insensitive. Exemplary polymers are (styrenic) block copolymers including A-B-A triblock structures. A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hotmelt are in the range of about 30 to about 60%, and the plasticizer has a low Mw of typically less than 1,000 and a Tg below room temperature, with a typical concentration of about 0 to about 15%.

The adhesive used for the fibrous layer preferably has elastomeric properties, such that the web formed by the fibers on the SAP is able to be stretched as SAP swell. Exemplary elastomeric, hotmelt adhesives include thermoplastic elastomers such as ethylene vinyl acetates, polyurethanes, polyolefin blends of a hard component (generally a crystalline polyolefin such as polypropylene or polyethylene) and a Soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer, mixtures of a thermoplastic elastomer and a low molecular weight resin modifier, e.g., a mixture of a styrene-isoprenes-tyrene block copolymer with polystyrene; and the elastomeric, hot-melt, pressure-sensitive adhesives described herein. Elastomeric, hot-melt adhesives of these types are described in more detail in U.S. Pat. No. 4,731,066 issued to Korpman on Mar. 15, 1988.

The thermoplastic adhesive material is applied as fibers. The fibers may exemplarily have an average thickness of about 1 to about 50 micrometers or about 1 to about 35 micrometers and an average length of about 5 mm to about 50 mm or about 5 mm to about 30 mm. To improve the adhesion of the thermoplastic adhesive material 4 to the second substrate 6 or to any other layer, in particular any other nonwoven layer, such layers may be pre-treated with an auxiliary adhesive. The fibers adhere to each other to form a fibrous layer, which can also be described as a mesh.

In certain embodiments, the thermoplastic adhesive material will meet at least one, or several, or all of the following parameters. An exemplary thermoplastic adhesive material may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more than 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

G' can be measured using a rheometer as indicated in WO2010/27719. The rheometer is capable of applying a shear stress to the adhesive and measuring the resulting strain (shear deformation) response at constant temperature. The adhesive is placed between a Peltier-element acting as lower, fixed plate and an upper plate with a radius R of e.g., 10 mm, which is connected to the drive shaft of a motor to generate the shear stress. The gap between both plates has a height H of e.g., 1500 micron. The Peltier-element enables temperature control of the material (±0.5° C.). The strain rate and frequency should be chosen such that all measurements are made in the linear viscoelastic region.

The thermoplastic adhesive material can be applied on the SAP by a thermoplastic adhesive material applicator which may be a nozzle system which can spray a relatively thin but wide curtain of thermoplastic adhesive material in fibrous form. The thermoplastic adhesive material may be applied at a basis weight of 1 gsm to 50 gsm, 5 to 20 gsm, e.g. 10 gsm in the area of the application of the thermoplastic adhesive material. The thermoplastic adhesive material may preferably cover at least the whole of the deposition area of the SAP, but it is also possible to cover a portion of or more than the deposition area of the SAP. The thermoplastic adhesive material can be applied at uniform basis weight over its area of application or it may applied with varying basis weight along the longitudinal axis L and/or transversal axis T (profiling in L or T direction).

Combination of the First Absorbent Layer 1 and Second Absorbent Layer 5

The first absorbent layer 1 and the second absorbent layer 5 are combined together such that at least a portion of the fibrous layer of thermoplastic adhesive material 4 of the second absorbent layer 5 contacts at least a portion of the layer of the cross-linked cellulose fibers 3 of the first absorbent layer 1.

FIG. 8 to 15 independently of each other show examples of combinations of the first and second absorbent structures, which may be used in combination with any of the features of the invention mentioned herein. The structure of the SAP layer is not detailed in these Figures, as any deposition pattern may be used within the SAP deposition area (e.g. transversal bars, dots, or continuous with no junction areas).

The absorbent core of the invention may comprise a shaped (non-rectangular) underlying SAP layer 7 and an overlying cross-linked cellulose layer 3, as shown for example on FIG. 9. Both the SAP layer and the cross-linked cellulose layer may also be shaped (non-rectangular), with a tapering deposition area in the area of the core intended to be placed at the crotch of the absorbent article where the core will be used, as shown on FIG. 10.

The core exemplarily shown in FIG. 11 is similar to the core of FIG. 10, with the cross-linked cellulose layer extending in the longitudinal direction to the edge of the underlying SAP layer. In general, the distribution area 8 of the SAP layer may be larger than the deposition area of the layer of cross-linked cellulose fibers. This may be advantageous as the SAP layer can more effectively retain fluid and provide dryness benefits. The cross-linked cellulose layer on the other hand may absorb fluid quicker than the SAP layer, and may be advantageously placed toward the wearer's side in the finished article. However the second absorbent layer can also be placed closer to the wearer side, which may provide better dryness of the product.

The core of the invention may have a rectangular SAP layer and a non-rectangular (shaped) cross-linked cellulose layer, as shown for example on FIG. 12. The core may also have a rectangular (non-shaped) cross-linked cellulose layer and a rectangular layer of SAP, as for example shown in FIG. 13.

The SAP layer 7 and/or the cross-linked cellulose layer 3 may be profiled along the longitudinal axis, so that the basis weight (amount deposited per unit of surface) of the SAP layer varies along the longitudinal axis (L). In particular it may be desirable to concentrate the absorbent materials close the area of insult, typically in the front area of the core. This is for example shown for both layers in FIG. 14.

The SAP layer 7 and/or the cross-linked cellulose layer 3 may also be profiled along the transversal axis, as shown for example in FIG. 15. The central part of the SAP layer, corresponding to the area of the longitudinal axis, may for example have a recess relative to the outwards area.

A further adhesive ("construction glue", not represented in the Figures) may be used to improve the adhesion of the first absorbent layer with the second absorbent layer. The construction glue may be any standard hotmelt glue as known in the art. If present, the construction glue may be typically sprayed on the whole or part of the surface of the layer of the cross-linked cellulose fibers or the fibrous adhesive layer before combining the two absorbent layers. The construction glue may be applied to the whole or only part of the surface of the layer of the cross-linked cellulose fibers, homogeneously or as a pattern. The application of a construction glue by spraying for example will only create discrete points of bonding which do not substantially impacts the passage of fluid between the absorbent layers contrary to a nonwoven layer.

If the fibrous thermoplastic adhesive material does not cover the whole of the surface of the second absorbent layer, for example if it is restricted to the whole or part of the SAP layer, then it may be advantageous to apply a construction glue at least in the areas of the second absorbent layer not contacting the fibrous thermoplastic adhesive material when both layers are combined, so that to improve the adherence also in these areas, such as the end seals of the core.

The invention can allow the production of cores with a profiled distribution of SAP at higher speed than conventional airfelt cores. The SAP in the second absorbent layer can be sufficiently immobilized using the physical entrapment offered by the thermoplastic adhesive material.

Channels

The SAP deposition area 8 may or may not comprise, in addition to the relatively small junction areas 10 described before, relatively large zones which are substantially free of SAP, and may take the form of channels. The layer of cross-linked cellulose fibers 3 may or may not also comprise such channels.

These channels may be particularly advantageous to help the fluid to penetrate quicker within the absorbent core. The first and/or second absorbent layer 1, 5 may comprise one or more channels, in particular one or more pairs of channels symmetrically arranged relative to the longitudinal axis L. Since the channels are substantially free of SAP, they will not swell when wet and will be typically clearly visible in wet state, whereas the junction areas which are much smaller and part of the deposition area may not be visible in wet state, as the SAP will expand and may swell into the junction areas.

The channels may in particular extend substantially longitudinally, which means typically that each channel extends more in the longitudinal direction than in the transverse direction, and typically at least twice as much in the longitudinal direction than in the transverse direction. The channels may also be present as one or several pairs in the absorbent layer, typically being symmetric along the longitudinal axis (i.e. taking the longitudinal axis as folding line). The first and second channels may be mirror images of one another with respect to the central longitudinal axis of the absorbent layer/core. In some embodiments, there may be no completely or substantially transverse channels present in at least said crotch region, or no such channels at all.

Thus, the channels may be completely longitudinal and parallel to the longitudinal direction of the absorbent layer (i.e. paralleled to said longitudinal-axis); but also may be curved, provided the radius of curvature is typically at least equal (and preferably at least 1.5 or at least 2.0 times this average transverse dimension) to the average transverse dimension of the absorbent layer; and also straight but under an angle of (e.g. from 5°) up to 30°, or for example up to 20°, or up to 10° with a line parallel to the longitudinal axis. This may also includes channels with an angle therein, provided said angle between two parts of a channel is at least 120°, preferably at least 150°; and in any of these cases, provided the longitudinal extension of the channel is more than the transverse extension.

Each of the channels may have an average width W' that is least 4% of the average width W of the absorbent layer in which they are present, or for example W' is at least 7% of W; and/or for example and up to 25% of W, or up to 15% of W; and/or for example at least 5 mm; and for example up to 25 mm, or for example up to 15 mm.

Each of said first and second channels may have an average length L' (as measured in the longitudinal direction) which may for example be up to 80% of the average length L of said absorbent layer in which they are present: if the channels are only in the front region, or only in the crotch region, or only in the back region, L' is for example up to 25% of L, or up to 20% of L, and/or L' is for example at least 5% of L, or at least 10% of L; and/or L' is for example at least 10 mm, or at least 20 mm, if the channels extend in said crotch region and front region, and optionally the back region, L' is for example up to 80% of L, or up to 70% of L, and/or L' is for example at least 40% of L, or at least 50% of L.

The channels are advantageously permanent channels, meaning their integrity is at least partially maintained both in the dry state and in the wet state. Permanent channels may be obtained by provision of one or more adhesive material, for example the fibrous layer of adhesive material 4 or a construction glue that helps adhering for example a substrate with an absorbent material within the walls of the channel. The Wet Channel Integrity Test described below can be used to test if channels are permanent following wet saturation and to what extent.

In the case where both absorbent layers comprise channels which at least partially correspond to each other, permanent channels may be in particular formed by bonding the first substrate and the second substrate together through the channels. Typically, an adhesive can be used to bond both substrate through the channels, but it is possible to bond via other known means, for example ultrasonic bonding, or heat bonding. This adhesive may for example comprise one or more auxiliary adhesive which can be applied to any of the substrate, as indicated before, and/or the fibrous layer (4) of thermoplastic adhesive material. The substrates can be continuously bonded or intermittently bonded along the channels.

Such channels may provide for fast liquid acquisition which reduces risk of leakages. The permanent channels help to avoid saturation of the absorbent layer in the region of fluid discharge (such saturation increases the risk of leakages). Furthermore, the inventors surprisingly found that, in contrast to what would be expected, whilst decreasing the overall amount of superabsorbent polymer material in the absorbent structure is reduced (by providing channels free of such material), the fluid handling properties of the absorbent structure, or diaper, are improved. Permanent channels, also have the further advantages that in wet state the absorbent material cannot move within the core and remains in its intended position, thus providing better fit and fluid absorption.

Advantageously, a permanent channel according to the invention has a percentage of integrity of at least 20%, or 30%, or 40%, or 50%, or 60, or 70%, or 80%, or 90% following the Wet Channel Integrity Test.

In some embodiments, there is no channel that coincides with the longitudinal axis L. The channels in a pair may be spaced apart from one another over their whole longitudinal dimension. The smallest spacing distance D may for example be at least 5% of average transverse dimension W of the corresponding absorbent layer, or for example at least 10% of W, or at least 15% of W; or for example may for example at least 5 mm, or for example at least 8 mm.

Furthermore, in order to reduce the risk of fluid leakages, the longitudinal main channels typically do not extend up to any of the transverse edges and/or longitudinal edges of the absorbent layer in which they are placed, as for example shown in the Figures. Typically, the smallest distance I between a channel and the nearest longitudinal edge and corresponds to at least 5% of W, or for example to at least 10% of W. In some embodiments, the distance is for example at least 10 mm; the smallest distance F between a channel and the nearest transverse edge of the absorbent layer may for example be at least 5% of the average length L of the layer.

The absorbent core may comprise only two channels, for example only in the front region, or for example in the middle (crotch) region, and optionally extending into the front and/or back region. The absorbent core may also comprise more than two of such channels, for example at least 4, or at least 5 or at least 6. Some or all of these may be substantially parallel to one another, for example being all straight and completely longitudinally, and/or two or more or all may be mirror images of one another in the longitudinal axis, or two or more may be curved or angled and fore example mirror images of one another in the longitudinal axis, and two or more may be differently curved or straight, and for example mirror images of one another in the longitudinal axis.

Shorter channels may also be present, for example in the front side of the core. The channels in the first absorbent layer may be registered with channels in the second absorbent layer if these are present. In that case the first and second substrate may be bonded through the channels via the fibrous adhesive layer 4 and/or a construction glue if present.

The channels may be particularly useful in the second absorbent layer when the deposition area of the SAP is rectangular, as the channels can improve the flexibility of the core to an extent that there is less advantage in using a non-rectangular (shaped) core. Of course channels may also be present in a layer of SAP having a shaped deposition area.

As indicated previously, the presence of channels in the first absorbent layer and/or the second absorbent layer is optional.

Method of Making the Core

Figure 16:
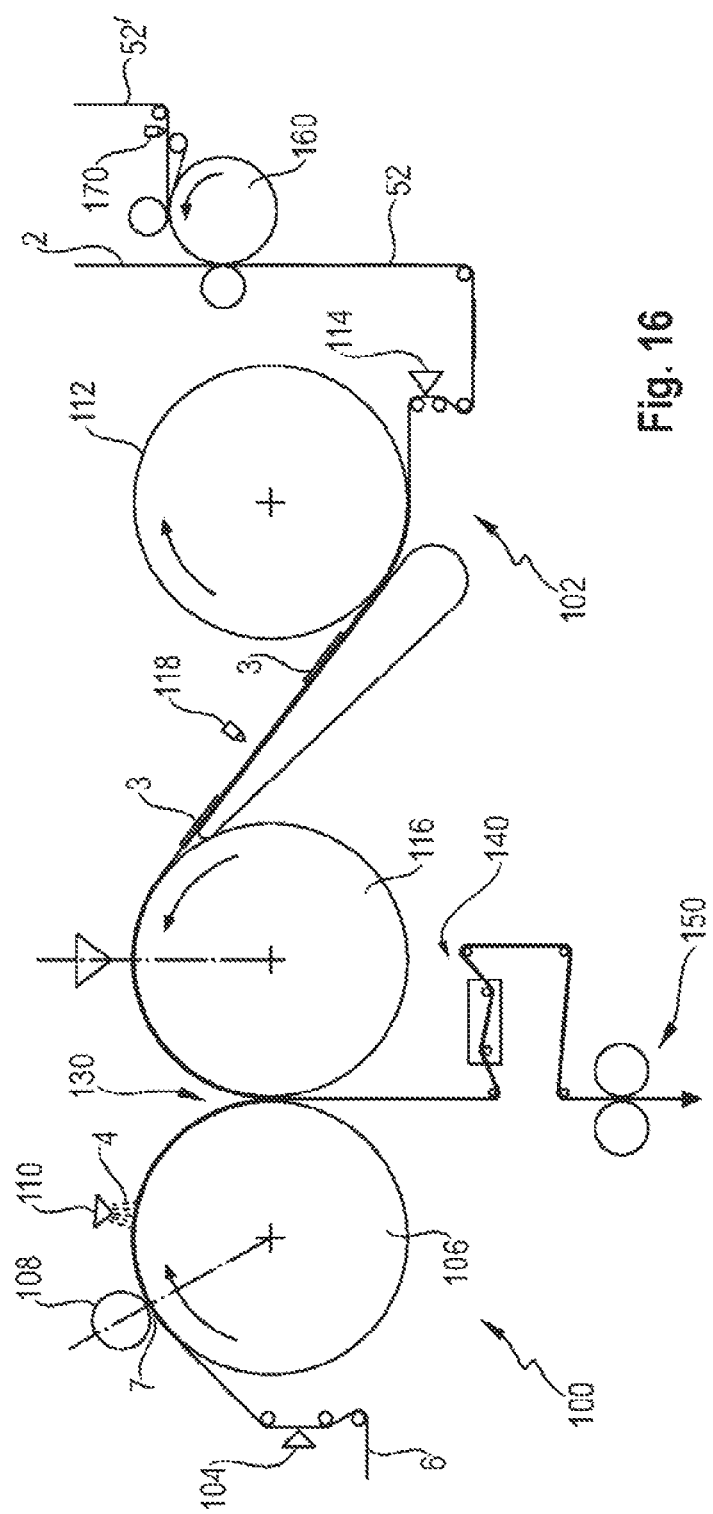
FIG. 16 shows a schematic diagram of a process for making a core according to the invention.

The absorbent cores of the invention may be made by any suitable methods, including hand made for research purpose. A particularly suitable process for industrial production combines a laying drum unit 102 for forming the first absorbent layer and a printing unit 100 for forming the second absorbent layer. Such an apparatus and method are exemplarily described with reference to FIG. 16.

The printing unit 100 may be similar to one of the printing units described in US2008/0312617A1. Such printing units may comprise an optional first auxiliary adhesive applicator 104 for applying an auxiliary adhesive to the second substrate 6, which may be a nonwoven web, a first rotatable support roll 106 for receiving the substrate 6, a hopper (not shown) for holding the superabsorbent particulate polymer material 7, a printing roll 108 for transferring the superabsorbent particulate polymer material 7 to the substrate 6, and a thermoplastic adhesive material applicator 110 for applying the fibrous layer of thermoplastic adhesive material 4 to the substrate 6 and the absorbent particulate polymer 7. A construction glue applicator (not shown) may be optionally used to further apply a construction glue on the second absorbent layer 5, for example in area of the second substrate where the fibrous layer of thermoplastic adhesive material 4 was not applied.

The laying drum unit 102 may comprise a second auxiliary adhesive applicator 114 for applying an optional auxiliary adhesive to the first substrate 2, and a lay down drum 112 for the cross-linked cellulose fibers 3. The supply of cross-linked cellulose fibers may be obtained by opening a supply of bailed fibers. After the layer of cross-linked cellulose fibers has been laid on the substrate 2, a construction glue may be applied on the first absorbent layer via a construction glue applicator 118, which can serve to improve the adhesion of the first absorbent layer with the second absorbent layer. The first absorbent layer is then conveyed to the vacuum drum 116, where it is combined with the second absorbent layer in a nip 130 formed by the rotatable support roll 106 and the vacuum roll 116.

A C-wrap device 140 may be used to C-wrap one of the substrate e.g. the first substrate around the core and against the second substrate, as detailed above. A pair of compression rolls 150 may be used to further bond the layers. Typically the cores of the invention can have a density of from 0.05 to 0.5 g/cm$^3$ at 0.2 psi after production, but other values are of course not excluded, for example further compression may happen when the core is integrated in an article or during packing of this article. The combined first and second absorbent layers can then be cut to form the individual cores ready to be integrated into a finished article.

The first and second auxiliary adhesive applicators 104 and 114 may be any suitable available glue applicator. The fibrous layer of thermoplastic adhesive material applicator 110 may for example comprise a nozzle system which can provide a relatively thin but wide curtain of thermoplastic adhesive material.

Further details of the construction of the printing unit are exemplarily given in 2008/0312617A1, see in particular FIG. 11-14 of this document and the corresponding description section. In particular, the rotatable support roll 106 may comprise a rotatable drum and a peripheral vented support grid for receiving the second substrate 6. The printing roll 108 can comprise a rotatable drum and a plurality of absorbent particulate polymer material reservoirs in a peripheral surface of the drum. The reservoirs may have a variety of shapes, including cylindrical, conical, or any other shape. The reservoirs may lead to an air passage in the drum and comprise a vented cover for holding adhesive particulate polymer material in the reservoir and preventing the adhesive particulate polymer material from falling or being pulled into the air passage.

In operation, the first and second substrates 2 and 6 may be received into the printing unit 100 and laying unit 102, respectively and further treated according to the following process. The second substrate 6 is drawn by the rotating support roll 106 past the first auxiliary adhesive applicator 104 which applies the first auxiliary adhesive to the second substrate 6 in a pattern. A vacuum (not shown) within the support roll 106 draws the second substrate 6 against the vertical support grid and holds the second substrate 6 against the first support roll 106. This presents an uneven surface on the substrate 2. Due to gravity, or by using the vacuum means, the substrate 2 will follow the contours of the uneven surface and thereby the substrate 2 will assume a mountain and valley shape. The SAP material 7 may accumulate in the valleys presented by the substrate 6. The support roll 106 then carries the second substrate 6 past the rotating printing roll 108 which transfers the absorbent particulate polymer material 7 from the hopper to the second substrate 6 in the grid pattern which is as illustrated in FIGS. 5 and 6 of 2008/0312617A1. A vacuum (not shown) in the printing roll 108 may hold the SAP 7 in the reservoirs until time to deliver the SAP 7 to the second substrate 6. The vacuum may then be released or air flow through the air passages may be reversed to eject the SAP 7 from the reservoirs and onto the second substrate 6. The SAP 7 may accumulate in the valleys presented by the substrate 6. The support roll 106 then carries the printed second substrate 6 past the thermoplastic adhesive material applicator 110 which applies the fibrous layer of thermoplastic adhesive material 4 to cover the SAP 7 on the second substrate 6.

Hence, the arrangement of reservoirs in the printing roll 108 and the uneven surface of the vented support grid of the support rolls 106 determine the distribution of SAP 7 throughout the second absorbent layer (land areas 9) and likewise determines the pattern of junction areas 10.

The process may also be used to directly combine an acquisition layer 52 with the absorbent core. The acquisition layer, which may be as indicated below a latex bonded nonwoven, may be fed from a roll as a continuous supply 52'. An acquisition layer adhesive may be applied using an acquisition layer adhesive applicator 170 and then fed into cut-and-space unit 160. The acquisition layer is cut to the right dimension and adhered to the side of the first substrate 2 which will be oriented externally in the finished core. As indicated previously, this acquisition layer is not part of the core of the invention as it placed externally to the core.

Absorbent Article 20

Although the absorbent core 28 of the present invention has been described until now in isolation from an absorbent article, it is expected that the absorbent core will be integrated within an absorbent article before being made available to the end user. Usually, but not necessarily, the absorbent core may be manufactured on the same production line as the rest of the absorbent article. It is also not excluded that the absorbent core of the invention may be used directly as an absorbent article without being assembled with further layers, for example if a more simple or cheaper article is desired. Within an absorbent article, the first absorbent layer of the absorbent core of the invention may be oriented towards the topsheet, so facing upwards when in use, as is represented in the Figures in the present application, but it is not excluded that the first absorbent layer be placed in the other direction with the first absorbent layer facing towards the backsheet.

Figure 19:
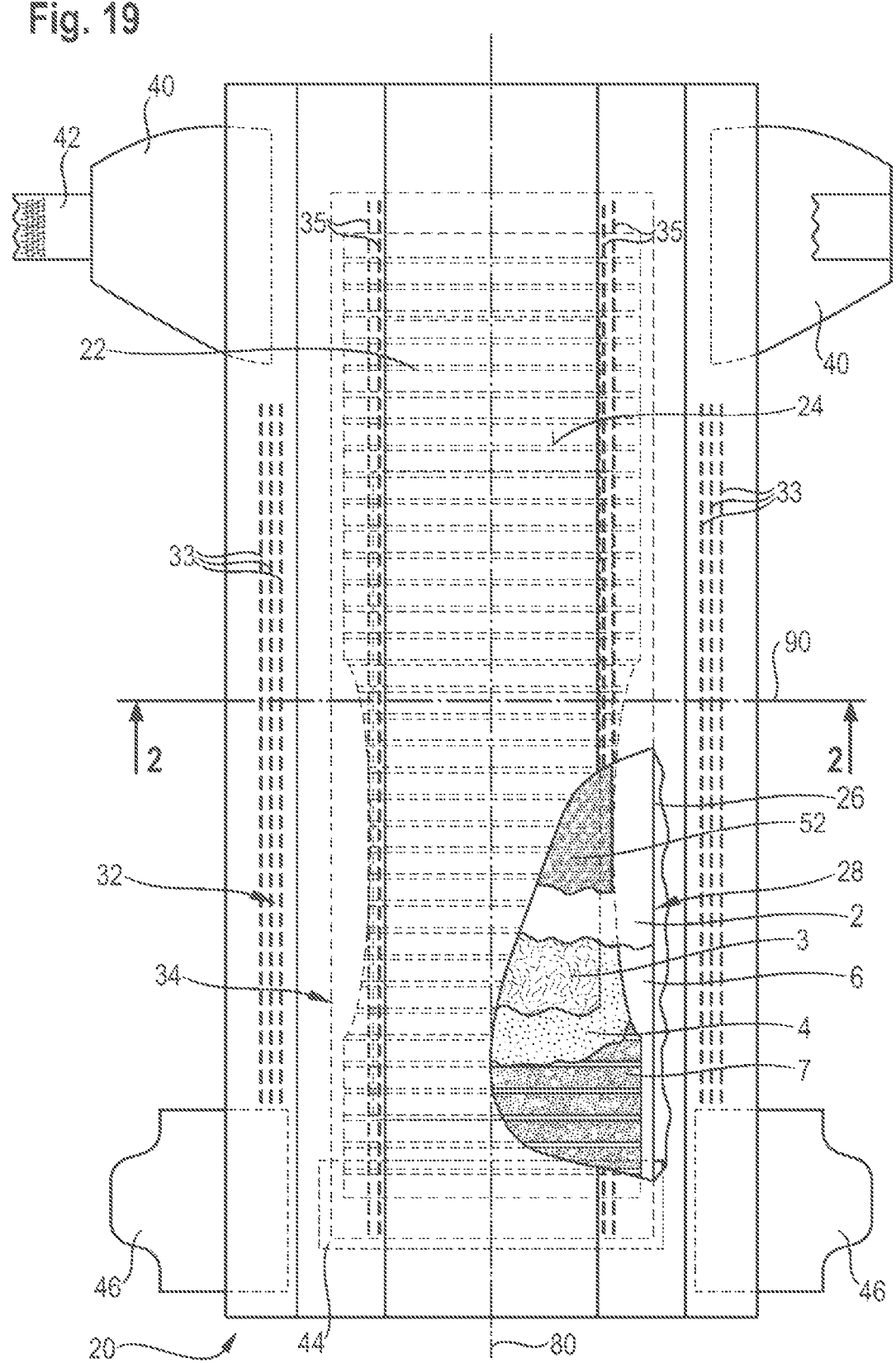
FIG. 19 shows the top view of a diaper comprising a core according to the invention, with some layers partially removed.
Figure 20:
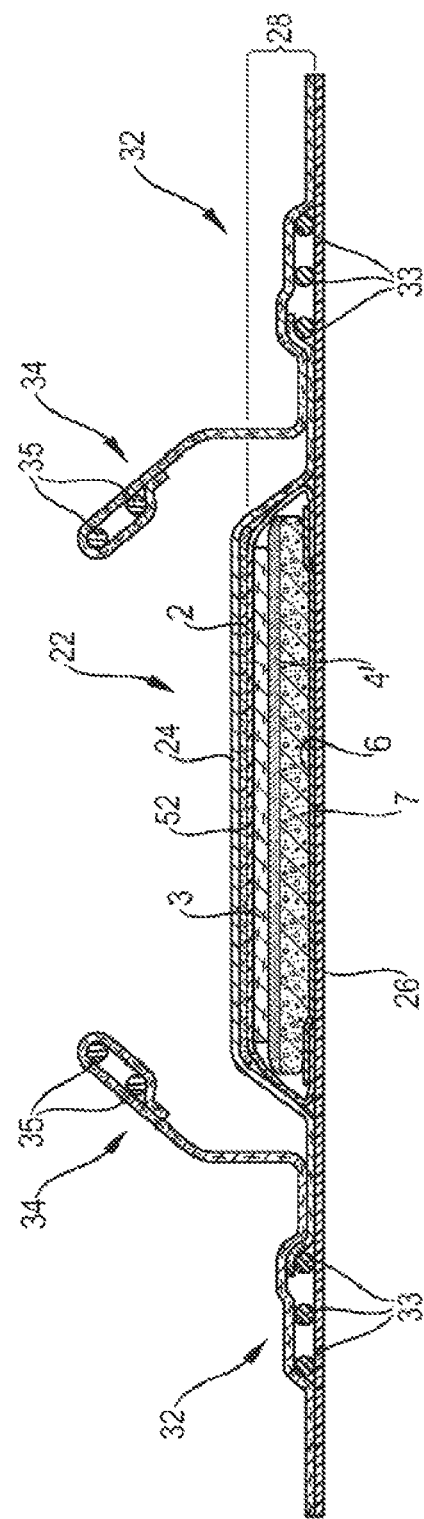
FIG. 20 shows the cross-section view in the transverse direction of a diaper comprising a core according to the invention.

An exemplary absorbent article in the form of an infant diaper 20 comprising an exemplary absorbent core of the invention is represented in FIGS. 19 and 20. In more details, FIG. 19 is a plan view of the exemplary diaper 20, in a flat-out state, with portions of the structure being cut-away to more clearly show the construction of the diaper 20. This diaper 20 is shown for illustration purpose only as the invention may be used for making a wide variety of diapers or other absorbent articles. In the following, the term "diaper" will be used for convenience, being understood that what follows can be applied to any other type of absorbent articles unless specifically excluded.

The absorbent article, here represented as a diaper, can comprise a liquid pervious topsheet 24, a liquid impervious backsheet 26, an absorbent core 28 placed between at least a portion of the topsheet 24 and the backsheet 26, an acquisition layer 52, elasticized leg cuffs 32 and barrier leg cuffs 34, and a fastening system which can comprise adhesive tabs 42 cooperating with a landing zone 44. The diaper may also comprise other elements, which are not represented, such as a back elastic waist feature, a front elastic waist feature, transverse barrier cuff(s), side panels or a lotion application.

The chassis 22 of the diaper 20 is the main body of the diaper and comprises the absorbent core 28 and preferably an outer covering including the topsheet 24 and/or the backsheet 26 and the acquisition layer 52. The diaper 20 may be unitary, so that the chassis 22 comprises the main structure of the diaper with other features such as back ears 40 and/or barrier cuffs 34 attached to it to form the composite diaper structure. The topsheet 24, the backsheet 26, and the absorbent core 28 may be assembled in a variety of well known configurations, in particular by gluing or heat embossing. Exemplary diaper configurations are described generally in U.S. Pat. No. 3,860, 003, 5,221,274 5,554,145, 5,569,234,5 ,580,411, and 6,004, 306.

The diaper may be notionally divided by a longitudinal centerline 80 and a transverse centerline 90, dividing the diapers in approximately equal section in each direction.

Backsheet 26

The backsheet 26 is generally that portion of the diaper 20 positioned adjacent the garment-facing surface of the absorbent core 28 and which prevents the exudates absorbed and contained therein from soiling articles such as bedsheets and undergarments. The backsheet 26 is typically impervious to liquids (e.g. urine). The backsheet may for example be or comprise a thin plastic film such as a thermoplastic film having a thickness of about 0.012 mm to about 0.051 mm. Exemplary backsheet films include those manufactured by Tredegar Corporation, based in Richmond, Va., and sold under the trade name CPC2 film. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585B2 to London Brown.

The backsheet 26 may be joined to the topsheet 24, the absorbent core 28 or any other element of the diaper 20 by any attachment means known in the art (as used herein, the term "joined" encompasses configurations whereby an element is directly secured to another element by affixing the element directly to the other element, and configurations whereby an element is indirectly secured to another element by affixing the element to intermediate member(s) which in turn are affixed to the other element). For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173, 4,785, 996; 4,842,666. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Topsheet 24

The topsheet 24 is the part of the absorbent article that is directly in contact with the wearer's skin. The topsheet can be attached to the backsheet, the core and/or any other layers as is known in the art. Suitable attachment means are described above with respect to means for joining the backsheet 26 to other elements of the diaper 20. Usually, the topsheet 24 and the backsheet 26 are joined directly to each other in some locations (e.g. on or close to the periphery of the diaper) and are indirectly joined together in other locations by directly joining them to one or more other elements of the diaper 20.

The topsheet 24 is preferably compliant, soft-feeling, and non-irritating to the wearer's skin. Further, at least a portion of the topsheet 24 is liquid pervious, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art, in particular spunbond PP nonwoven. One suitable topsheet 24 comprising a web of staple-length polypropylene fibers is manufactured by Veratec, Inc., a Division of International Paper Company, of Walpole, Mass. under the designation P-8.

Suitable formed film topsheets are described in U.S. Pat. Nos. 3,929,135, 4,324,246, 4,342,314, 4,463,045, and 5,006, 394. Other suitable topsheets 30 may be made in accordance with U.S. Pat. Nos. 4,609,518 and 4,629,643 issued to Curro et al. Such formed films are available from The Procter & Gamble Company of Cincinnati, Ohio as "DRI-WEAVE" and from Tredegar Corporation, based in Richmond, Va., as "CLIFF-T".

Any portion of the topsheet 24 may be coated with a lotion as is known in the art. Examples of suitable lotions include those described in U.S. Pat. Nos. 5,607,760, 5,609,587, 5,635, 5,643,588, 5,968,025 and 6,716,441. The topsheet 24 may also include or be treated with antibacterial agents, some examples of which are disclosed in PCT Publication WO95/ 24173. Further, the topsheet 24, the backsheet 26 or any portion of the topsheet or backsheet may be embossed and/or matte finished to provide a more cloth like appearance.

The topsheet 24 may comprise one or more apertures to ease penetration of exudates therethrough, such as urine and/ or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 $cm^2$ and about 50 $cm^2$, in particular between about 15 $cm^2$ and 35 $cm^2$. Examples of apertured topsheet are disclosed in U.S. Pat. No. 6,632,504, assigned to BBA NONWOVENS SIMPSON-VILLE. WO2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

Typical diaper topsheets have a basis weight of from about 10 to about 21 gsm, in particular between from about 12 to about 18 gsm but other basis weights are possible.

Acquisition Layer 52

The absorbent article of the invention may advantageously comprise an acquisition layer 52 placed between the absorbent core 28 and topsheet 24. The acquisition layer 52 may typically be or comprise a non-woven material, for example a SMS or SMMS material, comprising a spunbonded, a meltblown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round PET staple fibers (50/50 or 40/60 mix of 6 denier and 9 denier fibers). An exemplary binder is a butadiene/styrene latex.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co patent applications US2003/148684 to Cramer et al. and US2005/008839 to Cramer et al.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). In certain embodiments, the binder may be present in the upper acquisition layer 52 in excess of about 12%, about 14% or about 16% by weight. SB latex is available under the trade name GENFLO™ 3160 (OMNOVA Solutions Inc.; Akron, Ohio).

Unlike in some conventional diapers, the absorbent articles of the invention do not require a conventional lower acquisition layer placed between the acquisition layer 52 and the absorbent core 28. Typically, these lower acquisition layers would principally comprise cross-linked cellulose fibers, which have already been integrated in the present invention inside the core, so that this layer becomes unnecessary in the present invention.

Figure 17:
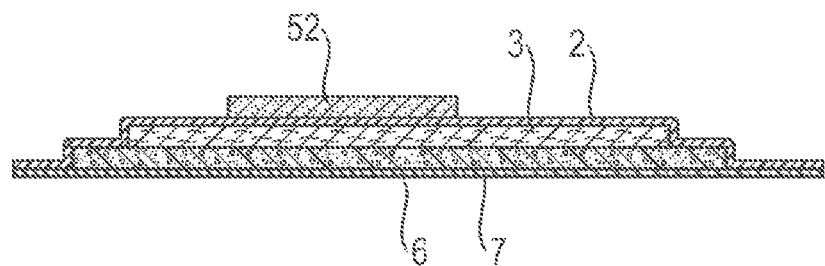
FIG. 17 shows a longitudinal cross-section of a core according to the invention with an acquisition layer placed above the layer of cross-linked cellulose.
Figure 18:
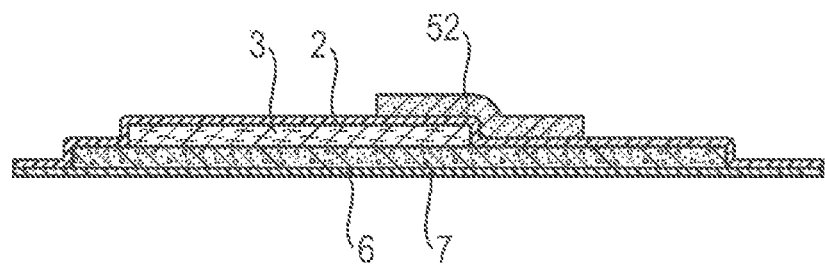
FIG. 18 shows a longitudinal cross-section of a core according to the invention with an acquisition layer placed partially above the layer of cross-linked cellulose and partially offset.

Furthermore, in one advantageous aspect of the invention and contrary to the acquisition layer of the prior art, as indicated in the Background Section, the acquisition layer 52 can be smaller than the layer of cross-linked cellulose 3. For example, as illustrated in FIG. 17, the acquisition layer 52 may be entirely placed above the layer of cross-linked cellulose 3 while being smaller (shorter, i.e. in the longitudinal direction as shown, or narrower, i.e. the lateral direction, or shorter and narrower). The acquisition layer 52 may also be placed partially or completely offset relative to the layer of cross-linked cellulose 3, as shown in FIG. 18 for example.

Fastening System 42, 44

The diaper 20 may also include a fastening system 42-44. The fastening system can be used to provide lateral tensions about the circumference of the diaper 20 to hold the diaper 20 on the wearer. The fastening system 42-44 usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the first waist region 36 for the fastener to be releasably attached. Some exemplary surface fastening systems are disclosed in U.S. Pat. Nos. 3,848,594, 4,662,875, 4,846,815, 4,894,060, 4,946,527, 5,151,092 and 5,221,274 issued to Buell. An exemplary interlocking fastening system is disclosed in U.S. Pat. No. 6,432,098. The fastening system 42-44 may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,736, and 5,591,152.

Front and Back Ears 46, 40

The diaper 20 may comprise front ears 46 and back ears 40 as is known in the art. The ears can be integral part of the chassis, for example formed from the topsheet and/or backsheet as side panel. Alternatively, as represented on FIG. 20, they may be separate elements attached by gluing and/or heat embossing. The back ears 40 are advantageously stretchable to facilitate the attachment of the tabs 42 on the landing zone 40 and maintain the taped diapers in place around the wearer's waist. The back ears 40 may also be elastic or extensible to provide a more comfortable and contouring fit by initially conformably fitting the diaper 20 to the wearer and sustaining this fit throughout the time of wear well past when the diaper 20 has been loaded with exudates since the elasticized ears allow the sides of the diaper 20 to expand and contract.

Leg Cuffs 32

The diaper 20 may comprise leg cuffs 32 which provide improved containment of liquids and other body exudates. Leg cuffs 32 may also be referred to as leg bands, side flaps, barrier cuffs, or elastic cuffs. Usually each leg cuff will comprise one or more elastic string 33, represented in exaggerated form on FIG. 20 comprised in the chassis of the diaper for example between the topsheet and backsheet in the area of the leg openings to provide an effective seal while the diaper is in use. It is also usual for the leg cuffs to comprise "stand-up" elasticized flaps (barrier leg cuffs) 34 which improve the containment of the leg regions. Each barrier leg cuff typically comprises one or more elastic strings 35.

U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. describe disposable diapers having "stand-up" elasticized flaps (barrier cuffs) which improve the containment of the leg regions. U.S. Pat. Nos. 4,695,278 and 4,795,454 issued to Lawson and to Dragoo respectively, describe disposable diapers having dual cuffs, including gasketing cuffs and barrier leg cuffs. In some embodiments, it may be desirable to treat all or a portion of the leg cuffs 32 with a lotion, as described above.

Elastic Waist Feature

The diaper 20 may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the end edge of the diaper 20. Disposable diapers can be constructed so as to have two elastic waist features, one positioned in the front waist region and one positioned in the back waist region 38. The elastic waist feature may be constructed in a number of different configurations including those described in U.S. Pat. Nos. 4,515,595, 4,710,189, 5,151,092 and 5,221,274.

Experimental Settings

Unless otherwise mentioned, the values indicated herein are measured according to the methods indicated herein below.

—Centrifuge Retention Capacity (CRC)

The CRC measures the liquid absorbed by the superabsorbent polymer particles for free swelling in excess liquid. The CRC is measured according to EDANA method WSP 241.2-05.

—Urine Permeability Measurement (UPM)
Urine Permeability Measurement System

This method determines the permeability of a swollen hydrogel (superabsorbent polymer) layer 1318. The equipment used for this method is described below. This method is closely related to the SFC (Salt Flow Conductivity) test method of the prior art.

Figure 21:
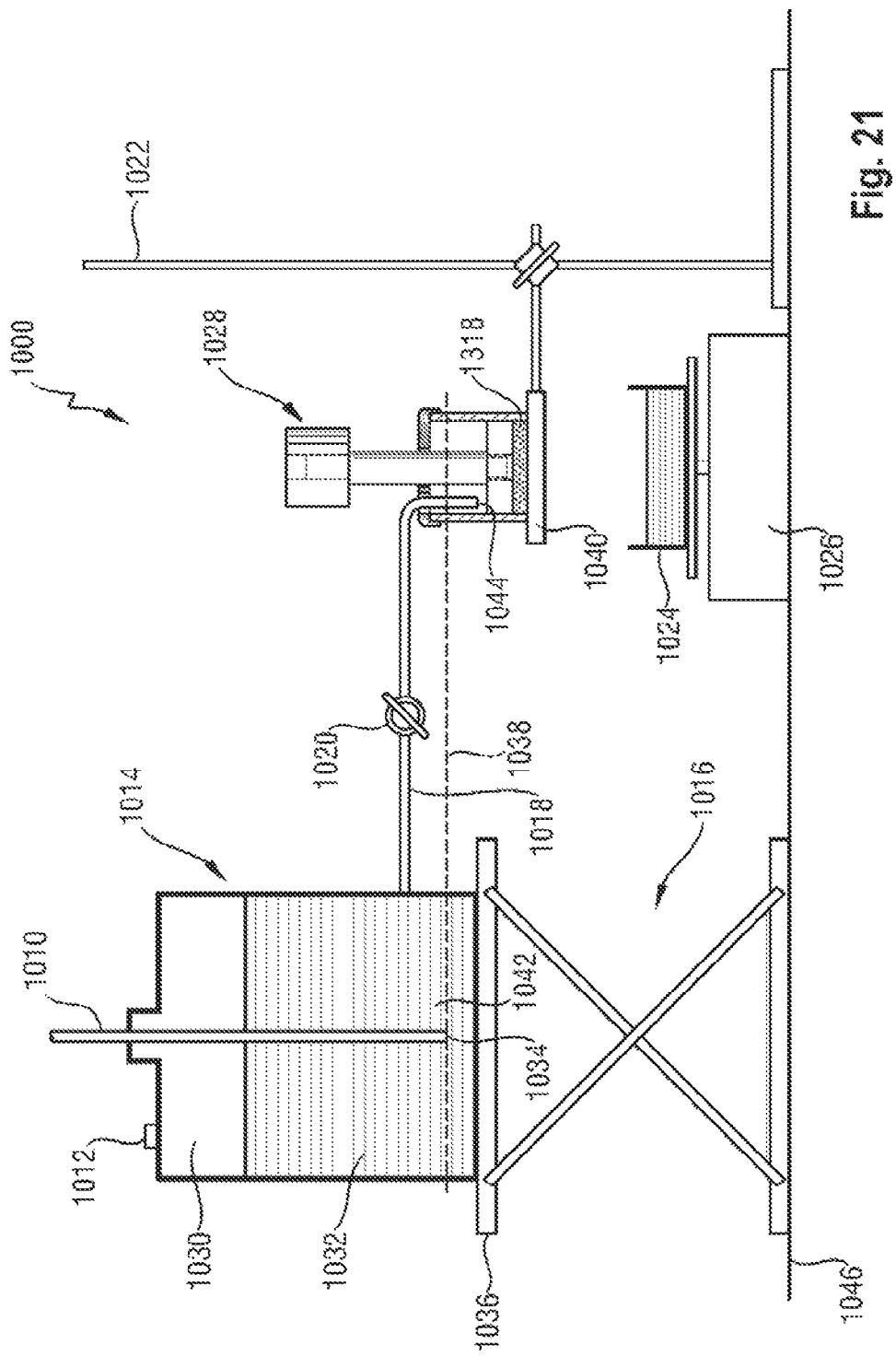
FIG. 21 is a partial cross-sectional side view of a suitable permeability measurement system for conducting the Urine Permeability Measurement Test.

FIG. 21 shows permeability measurement system 1000 set-up with the constant hydrostatic head reservoir 1014, open-ended tube for air admittance 1010, stoppered vent for refilling 1012, laboratory jack 1016, delivery tube 1018, stopcock 1020, ring stand support 1022, receiving vessel 1024, balance 1026 and piston/cylinder assembly 1028.

Figure 22:
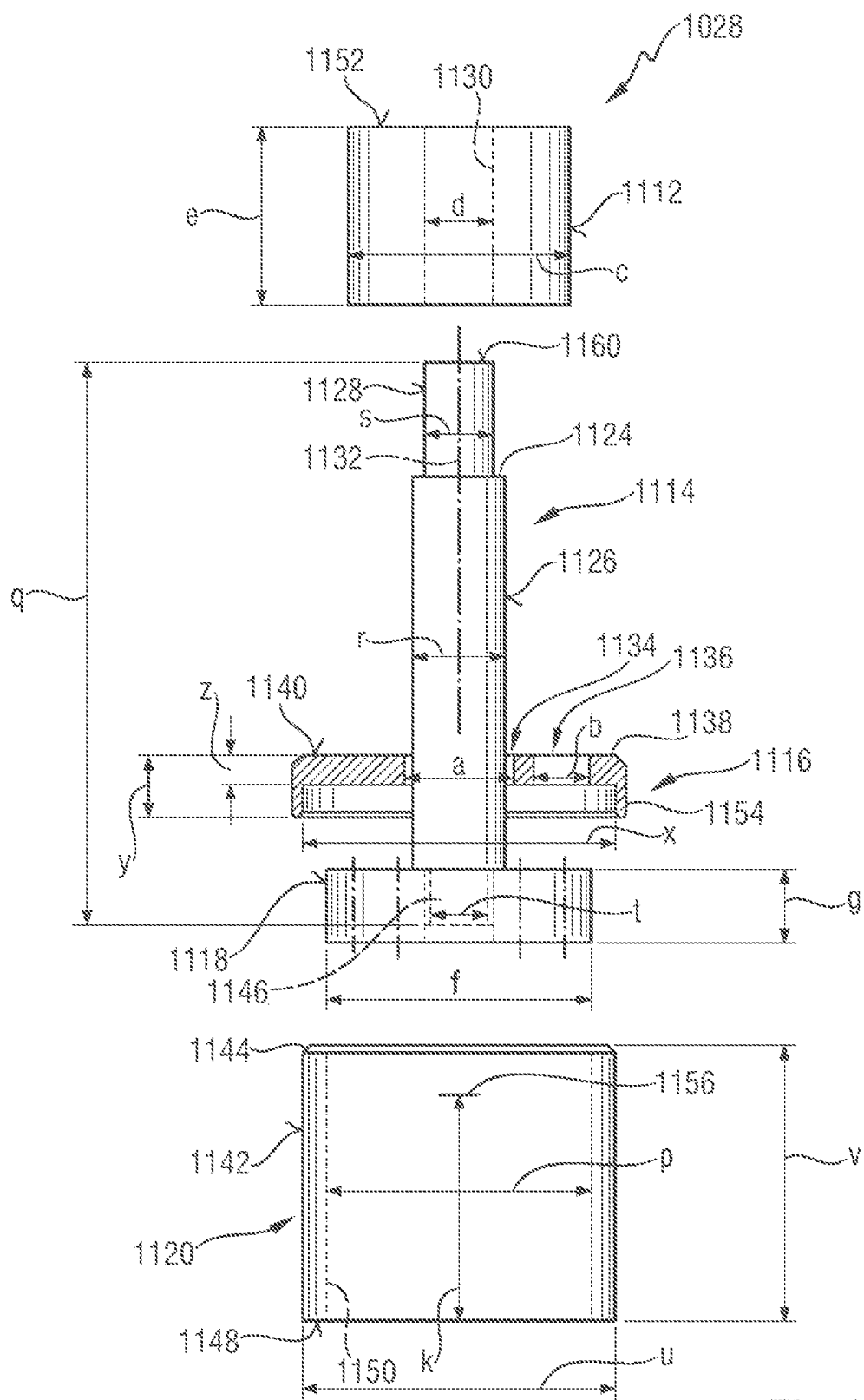
FIG. 22 is a cross-sectional side view of a piston/cylinder assembly for use in conducting the Urine Permeability Measurement Test.
Figure 23:
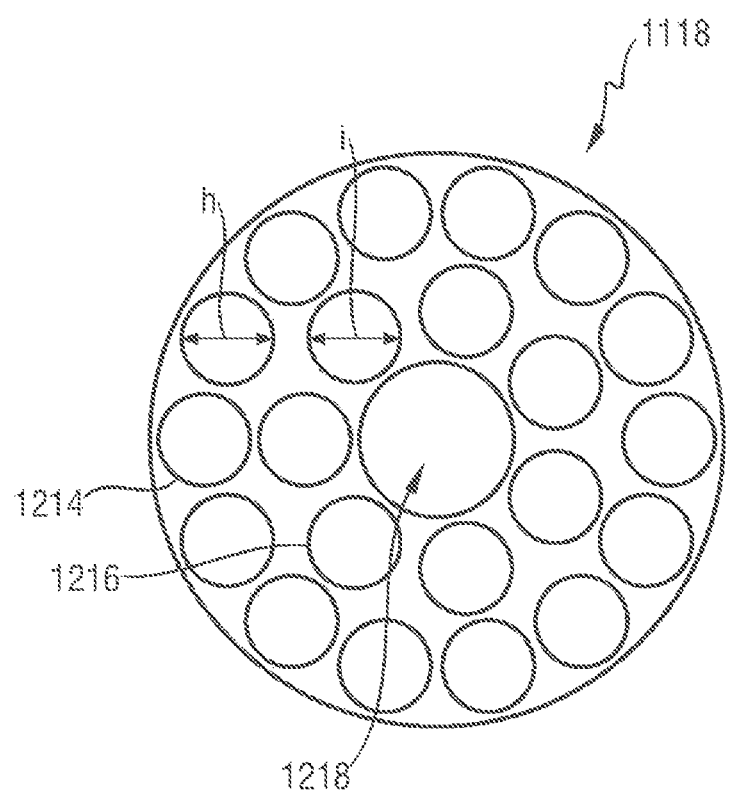
FIG. 23 is a top view of a piston head suitable for use in the piston/cylinder assembly shown in FIG. 22.
Figure 24:
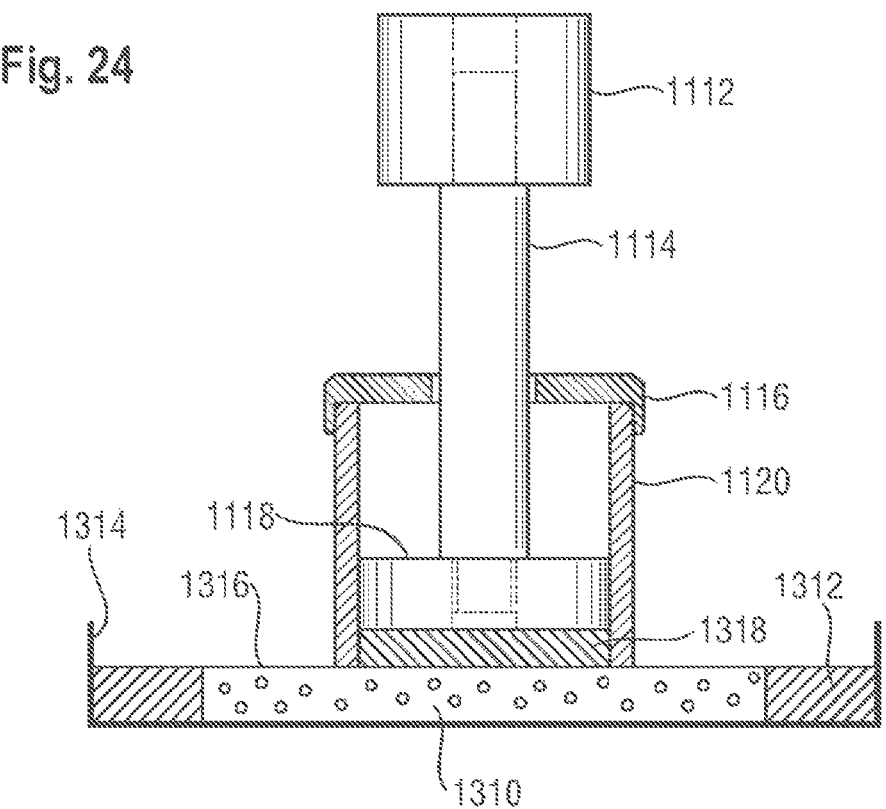
FIG. 24 is a cross-sectional side view of the piston/cylinder assembly of FIG. 22 placed on fritted disc for the swelling phase.

FIG. 22 shows the piston/cylinder assembly 1028 comprising a metal weight 1112, piston shaft 1114, piston head 1118, lid 1116, and cylinder 1120. The cylinder 1120 is made of transparent polycarbonate (e.g., Lexan®) and has an inner diameter p of 6.00 cm (area=28.27 cm$^2$) with inner cylinder walls 1150 which are smooth. The bottom 1148 of the cylinder 1120 is faced with a US. Standard 400 mesh stainless-steel screen cloth (not shown) that is bi-axially stretched to tautness prior to attachment to the bottom 1148 of the cylinder 1120. The piston shaft 1114 is made of transparent polycarbonate (e.g., Lexan®) and has an overall length q of approximately 127 mm. A middle portion 1126 of the piston shaft 1114 has a diameter r of 21.15 mm. An upper portion 1128 of the piston shaft 1114 has a diameter s of 15.8 mm, forming a shoulder 1124. A lower portion 1146 of the piston shaft 1114 has a diameter t of approximately ⅝ inch and is threaded to screw firmly into the center hole 1218 (see FIG. 21) of the piston head 1118. The piston head 1118 is perforated, made of transparent polycarbonate (e.g., Lexan®), and is also screened with a stretched US. Standard 400 mesh stainless-steel screen cloth (not shown). The weight 1112 is stainless steel, has a center bore 1130, slides onto the upper portion 1128 of piston shaft 1114 and rests on the shoulder 1124. The combined weight of the piston head 1118, piston shaft 1114 and weight 1112 is 596 g (±6 g), which corresponds to 0.30 psi over the area of the cylinder 1120. The combined weight may be adjusted by drilling a blind hole down a central axis 1132 of the piston shaft 1114 to remove material and/or provide a cavity to add weight. The cylinder lid 1116 has a first lid opening 1134 in its center for vertically aligning the piston shaft 1114 and a second lid opening 1136 near the edge 1138 for introducing fluid from the constant hydrostatic head reservoir 1014 into the cylinder 1120.

A first linear index mark (not shown) is scribed radially along the upper surface 1152 of the weight 1112, the first linear index mark being transverse to the central axis 1132 of the piston shaft 1114. A corresponding second linear index mark (not shown) is scribed radially along the top surface 1160 of the piston shaft 1114, the second linear index mark being transverse to the central axis 1132 of the piston shaft 1114. A corresponding third linear index mark (not shown) is scribed along the middle portion 1126 of the piston shaft 1114, the third linear index mark being parallel with the central axis 1132 of the piston shaft 1114. A corresponding fourth linear index mark (not shown) is scribed radially along the upper surface 1140 of the cylinder lid 1116, the fourth linear index mark being transverse to the central axis 1132 of the piston shaft 1114. Further, a corresponding fifth linear index mark (not shown) is scribed along a lip 1154 of the cylinder lid 1116, the fifth linear index mark being parallel with the central axis 1132 of the piston shaft 1114. A corresponding sixth linear index mark (not shown) is scribed along the outer cylinder wall 1142, the sixth linear index mark being parallel with the central axis 1132 of the piston shaft 1114. Alignment of the first, second, third, fourth, fifth, and sixth linear index marks allows for the weight 1112, piston shaft 1114, cylinder lid 1116, and cylinder 1120 to be re-positioned with the same orientation relative to one another for each measurement.

The cylinder 1120 specification details are:
Outer diameter u of the Cylinder 1120: 70.35 mm
Inner diameter p of the Cylinder 1120: 60.0 mm
Height v of the Cylinder 1120: 60.5 mm
The cylinder lid 1116 specification details are:
Outer diameter w of cylinder lid 1116: 76.05 mm
Inner diameter x of cylinder lid 1116: 70.5 mm
Thickness y of cylinder lid 1116 including lip 1154: 12.7 mm
Thickness z of cylinder lid 1116 without lip 1154: 6.35 mm
Diameter a of first lid opening 1134: 22.25 mm
Diameter b of second lid opening 1136: 12.7 mm
Distance between centers of first and second lid openings 1134 and 1136: 23.5 mm
The weight 1112 specification details are:
Outer diameter c: 50.0 mm
Diameter d of center bore 1130: 16.0 mm
Height e: 39.0 mm
The piston head 1118 specification details are
Diameter f: 59.7 mm
Height g: 16.5 mm
Outer holes 1214 (14 total) with a 9.65 mm diameter h, outer holes 1214 equally spaced with centers being 47.8 mm from the center of center hole 1218
Inner holes 1216 (7 total) with a 9.65 mm diameter i, inner holes 1216 equally spaced with centers being 26.7 mm from the center of center hole 1218
Center hole 1218 has a diameter j of ⅝ inches and is threaded to accept a lower portion 1146 of piston shaft 1114.

Prior to use, the stainless steel screens (not shown) of the piston head 1118 and cylinder 1120 should be inspected for clogging, holes or over-stretching and replaced when necessary. A urine permeability measurement apparatus with damaged screen can deliver erroneous UPM results, and must not be used until the screen has been replaced.

A 5.00 cm mark 1156 is scribed on the cylinder 1120 at a height k of 5.00 cm (±0.05 cm) above the screen (not shown) attached to the bottom 1148 of the cylinder 1120. This marks the fluid level to be maintained during the analysis. Maintenance of correct and constant fluid level (hydrostatic pressure) is critical for measurement accuracy.

A constant hydrostatic head reservoir 1014 is used to deliver salt solution 1032 to the cylinder 1120 and to maintain the level of salt solution 1032 at a height k of 5.00 cm above the screen (not shown) attached to the bottom 1148 of the cylinder 1120. The bottom 1034 of the air-intake tube 1010 is positioned so as to maintain the salt solution 1032 level in the cylinder 1120 at the required 5.00 cm height k during the measurement, i.e., bottom 1034 of the air tube 1010 is in approximately same plane 1038 as the 5.00 cm mark 1156 on the cylinder 1120 as it sits on the support screen (not shown) on the ring stand 1040 above the receiving vessel 1024. Proper height alignment of the air-intake tube 1010 and the 5.00 cm mark 1156 on the cylinder 1120 is critical to the analysis. A suitable reservoir 1014 consists of a jar 1030 containing: a horizontally oriented L-shaped delivery tube 1018 for fluid delivery, a vertically oriented open-ended tube 1010 for admitting air at a fixed height within the constant hydrostatic head reservoir 1014, and a stoppered vent 1012 for re-filling the constant hydrostatic head reservoir 1014. Tube 1010 has an internal diameter of 12.5 mm±0.5 mm. The delivery tube 1018, positioned near the bottom 1042 of the constant hydrostatic head reservoir 1014, contains a stopcock 1020 for starting/stopping the delivery of salt solution 1032. The outlet 1044 of the delivery tube 1018 is dimensioned to be inserted through the second lid opening 1136 in the cylinder lid 1116, with its end positioned below the surface of the salt solution 1032 in the cylinder 1120 (after the 5.00 cm height of the salt solution 1032 is attained in the cylinder 1120). The air-intake tube 1010 is held in place with an o-ring collar (not shown). The constant hydrostatic head reservoir 1014 can be positioned on a laboratory jack 1016 in order to adjust its height relative to that of the cylinder 1120. The components of the constant hydrostatic head reservoir 1014 are sized so as to rapidly fill the cylinder 1120 to the required height (i.e., hydrostatic head) and maintain this height for the duration of the measurement. The constant hydrostatic head reservoir 1014 must be capable of delivering salt solution 1032 at a flow rate of at least 3 g/sec for at least 10 minutes.

The piston/cylinder assembly 1028 is positioned on a 16 mesh rigid stainless steel support screen (not shown) (or equivalent) which is supported on a ring stand 1040 or suitable alternative rigid stand. This support screen (not shown) is sufficiently permeable so as to not impede salt solution 1032 flow and rigid enough to support the stainless steel mesh cloth (not shown) preventing stretching. The support screen (not shown) should be flat and level to avoid tilting the piston/cylinder assembly 1028 during the test. The salt solution 1032 passing through the support screen (not shown) is collected in a receiving vessel 1024, positioned below (but not supporting) the support screen (not shown). The receiving vessel 1024 is positioned on the balance 1026 which is accurate to at least 0.01 g. The digital output of the balance 1026 is connected to a computerized data acquisition system (not shown).

Preparation of Reagents (not illustrated)

Jayco Synthetic Urine (JSU) 1312 is used for a swelling phase (see UPM Procedure below) and 0.118 M Sodium Chloride (NaCl) Solution is used for a flow phase (see UPM Procedure below). The following preparations are referred to a standard 1 liter volume. For preparation of volumes other than 1 liter, all quantities are scaled accordingly.

JSU: A 1L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1L volume with distilled water. A stir bar is again inserted, and the solution stirred on a stirring plate for a few minutes more.

Quantities of salts to make 1 liter of Jayco Synthetic Urine:
Potassium Chloride (KCl) 2.00 g
Sodium Sulfate ($Na_2SO4$) 2.00 g
Ammonium dihydrogen phosphate ($NH_4H_2PO_4$) 0.85 g
Ammonium phosphate, dibasic (($NH_4$)$_2HPO_4$) 0.15 g
Calcium Chloride ($CaCl_2$) 0.19 g— [or hydrated calcium chloride ($CaCl_2.2H_2O$) 0.25 g]
Magnesium chloride ($MgCl_2$) 0.23 g— [or hydrated magnesium chloride ($MgCl_2.6H_2O$) 0.50 g]

To make the preparation faster, each salt is completely dissolved before adding the next one. Jayco synthetic urine may be stored in a clean glass container for 2 weeks. The solution should not be used if it becomes cloudy. Shelf life in a clean plastic container is 10 days.

0.118 M Sodium Chloride (NaCl) Solution: 0.118 M Sodium Chloride is used as salt solution 1032. Using a weighing paper or beaker 6.90 g (±0.01 g) of sodium chloride is weighed and quantitatively transferred into a 1L volumetric flask; and the flask is filled to volume with distilled water. A stir bar is added and the solution is mixed on a stirring plate until all the solids are dissolved.

Test Preparation

Using a solid reference cylinder weight (not shown) (40 mm diameter; 140 mm height), a caliper gauge (not shown) (e.g., Mitotoyo Digimatic Height Gage) is set to read zero. This operation is conveniently performed on a smooth and level bench top 1046. The piston/cylinder assembly 1028 without superabsorbent polymer particles is positioned under the caliper gauge (not shown) and a reading, $L_1$, is recorded to the nearest 0.01 mm.

The constant hydrostatic head reservoir 1014 is filled with salt solution 1032. The bottom 1034 of the air-intake tube 1010 is positioned so as to maintain the top part (not shown) of the liquid meniscus (not shown) in the cylinder 1120 at the 5.00 cm mark 1156 during the measurement. Proper height alignment of the air-intake tube 1010 at the 5.00 cm mark 1156 on the cylinder 1120 is critical to the analysis.

The receiving vessel 1024 is placed on the balance 1026 and the digital output of the balance 1026 is connected to a computerized data acquisition system (not shown). The ring stand 1040 with a 16 mesh rigid stainless steel support screen (not shown) is positioned above the receiving vessel 1024. The 16 mesh screen (not shown) should be sufficiently rigid to support the piston/cylinder assembly 1028 during the measurement. The support screen (not shown) must be flat and level.

UPM Procedure 1.5 g (±0.05 g) of superabsorbent polymer particles is weighed onto a suitable weighing paper or weighing aid using an analytical balance. The moisture content of the superabsorbent polymer particles is measured according to the Edana Moisture Content Test Method 430.1-99 ("Superabsorbent materials—Polyacrylate superabsorbent powders—Moisture Content—weight loss upon heating" (February 99)). If the moisture content of the superabsorbent polymer particles is greater than 5%, then the superabsorbent polymer particles weight should be corrected for moisture (i.e., in that particular case the added superabsorbent polymer particles should be 1.5 g on a dry-weight basis).

The empty cylinder 1120 is placed on a level benchtop 1046 and the superabsorbent polymer particles are quantitatively transferred into the cylinder 1120. The superabsorbent polymer particles are evenly dispersed on the screen (not shown) attached to the bottom 1148 of the cylinder 1120 by gently shaking, rotating, and/or tapping the cylinder 1120. It is important to have an even distribution of particles on the screen (not shown) attached to the bottom 1148 of the cylinder 1120 to obtain the highest precision result. After the superabsorbent polymer particles have been evenly distributed on the screen (not shown) attached to the bottom 1148 of the cylinder 1120 particles must not adhere to the inner cylinder walls 1150. The piston shaft 1114 is inserted through the first lid opening 1134, with the lip 1154 of the lid 1116 facing towards the piston head 1118. The piston head 1118 is carefully inserted into the cylinder 1120 to a depth of a few centimeters. The lid 1116 is then placed onto the upper rim 1144 of the cylinder 1120 while taking care to keep the piston head 1118 away from the superabsorbent polymer particles. The lid 1116 and piston shaft 1126 are then carefully rotated so as to align the third, fourth, fifth, and sixth linear index marks are then aligned. The piston head 1118 (via the piston shaft 1114) is then gently lowered to rest on the dry superabsorbent polymer particles. The weight 1112 is positioned on the upper portion 1128 of the piston shaft 1114 so that it rests on the shoulder 1124 such that the first and second linear index marks are aligned. Proper seating of the lid 1116 prevents binding and assures an even distribution of the weight on the hydrogel layer 1318.

Swelling Phase: An 8 cm diameter fritted disc (7 mm thick; e.g. Chemglass Inc. #CG 201-51, coarse porosity) 1310 is saturated by adding excess JSU 1312 to the fritted disc 1310 until the fritted disc 1310 is saturated. The saturated fritted disc 1310 is placed in a wide flat-bottomed Petri dish 1314 and JSU 1312 is added until it reaches the top surface 1316 of the fritted disc 1310. The JSU height must not exceed the height of the fitted disc 1310.

The screen (not shown) attached to the bottom 1148 of the cylinder 1120 is easily stretched. To prevent stretching, a sideways pressure is applied on the piston shaft 1114, just above the lid 1116, with the index finger while grasping the cylinder 1120 of the piston/cylinder assembly 1028. This "locks" the piston shaft 1114 in place against the lid 1116 so that the piston/cylinder assembly 1028 can be lifted without undue force being exerted on the screen (not shown).

The entire piston/cylinder assembly 1028 is lifted in this fashion and placed on the fritted disc 1310 in the Petri dish 1314. JSU 1312 from the Petri dish 1314 passes through the fritted disc 1310 and is absorbed by the superabsorbent polymer particles (not shown) to form a hydrogel layer 1318. The JSU 1312 available in the Petri dish 1314 should be enough for all the swelling phase. If needed, more JSU 1312 may be added to the Petri dish 1314 during the hydration period to keep the JSU 1312 level at the top surface 1316 of the flitted disc 1310. After a period of 60 minutes, the piston/cylinder assembly 1028 is removed from the fritted disc 1310, taking care to lock the piston shaft 1114 against the lid 1116 as described above and ensure the hydrogel layer 1318 does not lose JSU 1312 or take in air during this procedure. The piston/cylinder assembly 1028 is placed under the caliper gauge (not shown) and a reading, $L_2$, is recorded to the nearest 0.01 mm. If the reading changes with time, only the initial value is recorded. The thickness of the hydrogel layer 1318, $L_0$ is determined from $L_2$-$L_1$ to the nearest 0.1 mm.

The piston/cylinder assembly 1028 is transferred to the support screen (not shown) attached to the ring support stand 1040 taking care to lock the piston shaft 1114 in place against the lid 1116. The constant hydrostatic head reservoir 1014 is positioned such that the delivery tube 1018 is placed through the second lid opening 1136. The measurement is initiated in the following sequence:

a) The stopcock 1020 of the constant hydrostatic head reservoir 1014 is opened to permit the salt solution 1032 to reach the 5.00 cm mark 1156 on the cylinder 1120. This salt solution 1032 level should be obtained within 10 seconds of opening the stopcock 1020.

b) Once 5.00 cm of salt solution 1032 is attained, the data collection program is initiated.

With the aid of a computer (not shown) attached to the balance 1026, the quantity of salt solution 1032 passing through the hydrogel layer 1318 is recorded at intervals of 20 seconds for a time period of 10 minutes. At the end of 10 minutes, the stopcock 1020 on the constant hydrostatic head reservoir 1014 is closed.

The data from 60 seconds to the end of the experiment are used in the UPM calculation. The data collected prior to 60 seconds are not included in the calculation. The flow rate $F_s$ (in g/s) is the slope of a linear least-squares fit to a graph of the weight of salt solution 1032 collected (in grams) as a function of time (in seconds) from 60 seconds to 600 seconds.

The Urine Permeability Measurement (Q) of the hydrogel layer 1318 is calculated using the following equation:

$$Q=[F_g \times L_0]/[\rho \times A \times \Delta P],$$

where $F_g$ is the flow rate in g/sec determined from regression analysis of the flow rate results, $L_0$ is the initial thickness of the hydrogel layer 1318 in cm, $\rho$ is the density of the salt solution 1032 in g/cm$^3$. A (from the equation above) is the area of the hydrogel layer 1318 in cm$^2$, $\Delta P$ is the hydrostatic pressure in dyne/cm$^2$, and the Urine Permeability Measurement, Q, is in units of cm$^3$ sec/g. The average of three determinations should be reported.

Wet Channel Integrity Test

This test is designed to check the integrity of a channel following wet saturation. The test can be performed directly on an absorbent core. If an absorbent article is provided and the core is not available separately, the test can be performed on the absorbent article after removing the topsheet and any other intermediate layers for example acquisition layers, surge layers etc.

1. The length (in millimeters) of the channel is measured in the dry state (if the channel is not straight, the curvilinear length through the middle of the channel is measured).
2. The absorbent core is then immersed in 5 liters of synthetic urine "Saline", with a concentration of 9.00 g NaCl per 1000 ml solution prepared by dissolving the appropriate amount of sodium chloride in distilled water. The temperature of the solution must be 20+/−5° C.
3. After 1 minute in the saline, the absorbent core is removed and held vertically by one end for 5 seconds to drain, then extended flat on a horizontal surface with the garment-facing side down, if this side is recognizable. If the absorbent core comprises stretch elements, the absorbent core is pulled taut in both X and Y dimensions so that no contraction is observed. The extremes/edges of the absorbent core are fixed to the horizontal surface, so that no contraction can happen.
4. The absorbent core is covered with a suitably weighted rigid plate, with dimensions as follows: length equal to the extended length of the absorbent core, and width equal to the maximum absorbent core width in the cross direction.
5. A pressure of 18.0 kPa is applied for 30 seconds over the area of the rigid plate above mentioned. Pressure is calculated on the basis of overall area encompassed by the rigid plate. Pressure is achieved by placing additional weights in the geometric center of the rigid plate, such that the combined weight of the rigid plate and the additional weights result in a pressure of 18.0 kPa over the total area of the rigid plate.
6. After 30 seconds, the additional weights and the rigid plate are removed.
7. Immediately afterwards, the cumulative length of the portions of the channel which remained intact by visual determination is measured (in millimeters; if the channel is not straight, the curvilinear length through the middle of the channel is measured). If no portions of the channel remained intact then the channel is not permanent.
8. The percentage of integrity of the permanent channel is calculated by dividing the cumulative length of the portions of the channel which remained intact by the length of the channel in the dry state, and then multiplying the quotient by 100.

—Run-off Test Method

The Run-off Test Method is intended to test whether the test liquid gets absorbed quickly enough into the diaper as opposed to running-off over the surface of the topsheet and leaking at the back edge of the diaper. This method determines the liquid run-off of a baby diaper typically designated for wearers having a weight in the range of 8 to 13 kg±20% (such as Pampers Active Fit size 4 or other Pampers baby diapers size 4, Huggies baby diapers size 4 or baby diapers size 4 of most other tradenames). All testing is carried out at 23±2° C. and 40-55% relative humidity.

The test apparatus comprises an angled table made of polycarbonate (e.g. Lexan®) about 10 mm in thickness. The angled table is 520 mm long and 160 mm wide and is inclined by 30±1 degrees vs. horizontal: the dimensions of the table can be adjusted such to be larger than the diaper dimensions. The angled table is attached to a support, made of polycarbonate (e.g. Lexan®) about 10 mm in thickness or an equivalent suitable material.

A diaper is removed from its packaging and the cuff elastics are cut at suitable intervals to allow the product to lay flat: it must be taken care to touch the topsheet as little as possible and not to damage the diaper core. The product is weighed to within ±0.1 grams on a suitable top-loading balance then attached via bi-adhesive tape onto angled table such that the product is centered along the longitudinal centerline of the apparatus with the topsheet (body-side) of the product facing upwards, its front waist edge standing on the upper part of the angled table and its back edge being in line with the lower edge of the angled table: the loading point is marked onto the product via a water resistant pen at a position 102 mm from the front core absorbent edge.

A suitable pump; e.g. Model 7520-00 supplied by Cole Parmer Instruments, Chicago, USA, or equivalent; is set up to discharge a 0.9 mass % aqueous solution of sodium chloride through a flexible plastic tube having an internal diameter of 4.8 mm, e.g Tygon® R-3603 or equivalent. The end portion of the tube is clamped vertically so that it is centered vertically 25 mm above the loading point marked onto the product: the position of the end portion of the tube is adjusted after each gush such to maintain the distance of 25 mm above the loading point marked onto the product. The pump is operated via a timer and is pre-calibrated to discharge a gush of 75.0 ml of the 0.9% saline solution at a rate of 15 mlisec. Four gushes are delivered to the product in this fashion; the time interval between the beginning of a certain gush and the beginning of the next gush is 300 seconds.

A suitable Petri dish is pre-weighted and placed under the lower edge of the angled table to collect the run-off liquid. The test liquid run-off is calculated after each gush via subtracting the weight of the Petri dish with run-off liquid and the dry weight of the Petri dish. The total test liquid run-off is also reported and calculated as the sum of the first, second, third and fourth gush run-off. After each gush a dry Petri dish is used. Four products for each option are tested in this fashion and the average for each of the respective gushes (first through fourth) and for the total run-off is calculated.

EXAMPLES

Diaper prototypes have been produced using Pampers Baby Dry size 4 diapers commercially available in Germany in April 2012 and replacing the storage core and acquisition patch.

Comparative Example 1

The first substrate used (in this section "core cover") was a hydrophilic coated PP (polypropylene) nonwoven material, with Spunbonded, Meltblown, Meltblown, and Spunbonded layers forming an SMMS structure. The basis weights of the M-layers are 2 gsm and the S-Layers 8 gsm, resulting in a material with an overall basis weight of 10 gsm. The material is coated with PHP26 (Schill&Seilacher) with an add on level between 0.5-0.8% (EDANA WSP 353.0 (08)) to be hydrophilic. The core cover has a width 165 mm and a length of 440 mm.

The second substrate used (in this section "dusting layer") was a hydrophobic non-coated PP nonwoven material, with Spunbonded, Meltblown, Meltblown, and Spunbonded layers forming an SMMS structure. The basis weights of the M-layers are 2 gsm and the S-Layers 8 gsm, resulting in a material with an overall basis weight of 10 gsm. The dusting layer has a width of 130 mm and a length of 440 mm.

Glue HL1358LO available from HB Fuller was applied onto the nonwoven dusting layer as 41 slots each 1 mm wide and spaced by 1 mm such to cover a pattern 81 mm wide and 440 mm long centered versus the longitudinal axis of the core, such that the glue basis weight has been 5 gsm in the glue covered area. This glue application is called herein auxiliary glue.

Glue HL1358LO available from HB Fuller was further applied to provide end seals of the core onto the nonwoven dusting layer as 60 slots each 1 mm wide and spaced by 1 mm such to cover a pattern 119 mm wide and 30 mm long centered versus the longitudinal axis of the core, such that the glue basis weight has been 40 gsm in the glue covered area, starting 15 mm before absorbent core front end and as 60 slots each 1 mm wide and spaced by 1 mm such to cover a pattern 119 mm wide and 25 mm long centered versus the longitudinal axis of the core, such that the glue basis weight has been 40 gsm in the glue covered area, starting 400 mm from absorbent core front end. This glue adheres both substrates directly together to provide end sealing of the core.

The SAP layer was bonded to the auxiliary glue. The SAP layer was made with AQUALIC CA (Type L597) with CRC of 26.8 g/g and UPM of 108 $10^{-7}$ $cm^3$ s/g. A total of 14.6 g of SAP has been used. The SAP layer was 410 mm long and had a width of 110 mm. The SAP amount was distributed along the longitudinal axis of the core as follows: 5.1 g of SAP from the absorbent core front edge until a distance of 110 mm from the absorbent core front edge, 5.7 g of SAP between 110 mm and 220 mm from the absorbent core front edge, 2.9 g of SAP between 220 mm and 330 mm from the front edge, 0.9 g of SAP between 330 mm and 410 mm from the absorbent core front edge. The SAP layer was placed onto the nonwoven dusting layer such that the nonwoven dusting layer is at front and back 15 mm longer than the SAP layer.

The SAP was applied in the transversal bar pattern, with bars being 10 mm wide and having a distance of about 2 mm between each bar. The microfiber glue NW 1151 ex HB Fuller was applied onto the SAP layer in a fibrous adhesive layer pattern having a width of 108 mm, a length of 440 mm and a basis weight of 17.5 gsm, the pattern being symmetric versus the longitudinal axis of the core.

The SAP layer was bonded to nonwoven core cover with a glue layer of construction glue DM519a ex available from Henkel, in a fibrous adhesive layer pattern having a width of 108 mm, a length of 440 mm and a basis weight of 4 gsm, being the pattern symmetric versus the longitudinal axis of the core.

The core was sealed with 2 continuous lines of adhesive applied onto the nonwoven core cover at a distance of 140 mm, each line having a length of 440 mm a basis weight such that the amount of applied glue for both lines is 140 mg. As adhesive HL1358LO ex HB Fuller was used and the core cover was folded to a width of 120 mm such that the 2 adhesive glue lines have been attached to the nonwoven dusting layer.

The nonwoven dusting layer and nonwoven core cover had the same length and were positioned such that they overlapped in the longitudinal axis of the core.

An acquisition patch was made of a layer of crosslinked cellulosic fibers and an acquisition layer. The acquisition layer was a carded, resin-bonded nonwoven with a basis weight of 43 gsm consisting of fibers of solid round PET staple fibers (50/50 or 40/60 mix of 6 denier and 9 denier fibers) and a binder consisting of butadiene/styrene latex.

The crosslinked cellulosic fiber layer can be prepared as described in EP 765174B1. The crosslinked cellulosic fiber layer had a total amount of 4.46 g crosslinked cellulosic fibers, was 298 mm long and had a width of 80 mm, starting at 28 mm from absorbent core front edge. The crosslinked cellulosic fiber amount was distributed along the longitudinal axis of the layer homogeneously, such that, if divided into three parts of equivalent length, i.e. 99 mm, each part of the layer contained 1.49 g crosslinked cellulosic fibers. The crosslinked cellulosic fiber layer was attached to the acquisition layer with glue DM519a ex available from Henkel, applied as 6 slots each 4 mm wide and spaced by 9 mm such to cover a pattern 69 mm wide and 298 mm long, such that the glue basis weight has been 2.2 gsm in the glue covered area.

The acquisition patch was glued with glue spirals of hot melt adhesive/PA—Bostik (H2031F) with Basis weight of 5 gsm onto the nonwoven core cover such that the crosslinked cellulosic fiber layer faced the nonwoven core cover and the acquisition patch started 28 mm from absorbent core front edge. The area covered with glue spirals was 65 mm wide, 288 mm long and starts 33 mm from absorbent core front edge.

The storage core with acquisition patch made as described above was used to replace the storage core and acquisition patch in a Pampers Baby Dry size 4 diaper commercially available in Germany in April 2012. These were compacted in a bag at an In Bag Stack Height, i.e. the total caliper of 10 bi-folded diapers, of 67 mm for 6 days, had then been taken out of the bag for 1 day in the laboratory, loosely stored in a closed plastic bag (e.g. ex VWR International, Druckverschlußbeutel, 400 mm×500 mm, HG #210150 No 102.550 or equivalent), before being analyzed.

Comparative Example 2

This is as Comparative example 1 with the only difference being that the crosslinked cellulosic fiber layer had a total amount of 5.65 g crosslinked cellulosic fiber. The crosslinked cellulosic fiber amount was distributed along the longitudinal axis of the layer homogeneously, such that, if divided into three parts of equivalent length, i.e. 99 mm, each part of the layer contained 1.88 g crosslinked cellulosic fibers.

Invention Example

The core's first and second substrates were the same as respectively the core cover and dusting layer referred to above in the comparative examples. The SAP layer was made and bonded to the nonwoven dusting layer in the same way as for the comparative examples.

The SAP layer was bonded to a crosslinked cellulosic fiber layer with a glue layer of construction glue DM519a ex available from Henkel, in a fibrous adhesive layer pattern having a width of 108 mm, a length of 440 mm and a basis weight of 4 gsm, the pattern being symmetric versus the longitudinal axis of the core. The construction glue was applied uniformly onto the crosslinked cellulosic fiber layer.

The crosslinked cellulosic fiber layer can be prepared as described in EP 765174B1. The crosslinked cellulosic fiber layer had a total amount of 4.4 g crosslinked cellulosic fibers, was 298 mm long and had a width of 80 mm, starting at 28 mm from absorbent core front edge. The crosslinked cellulosic fiber amount was distributed along the longitudinal axis of the layer as follows: 1.36 g of crosslinked cellulosic fiber from the absorbent core front edge until a distance of 110 mm from the absorbent core front edge, 1.87 g of crosslinked cellulosic fiber between 110 mm and 220 mm from the absorbent core front edge, 1.20 g of crosslinked cellulosic fiber between 220 mm and 330 mm from the front edge. The crosslinked cellulosic fiber layer was attached to the nonwoven core cover with glue DM519a ex available from Henkel, applied as 8 slots each 3 mm wide and spaced by 8 mm such to cover a pattern 80 mm wide and 294 mm long, starting at 26 mm from absorbent core front edge, centered versus the longitudinal axis of the core, such that the glue basis weight was 4.2 gsm in the glue covered area.

The core was sealed as described for the comparative examples.

The nonwoven dusting layer and nonwoven core cover had the same length and were positioned such that they overlap in the longitudinal axis of the core.

Onto the nonwoven core cover an acquisition layer of 90 mm width and 243 mm length was placed, starting 28 mm from absorbent core front edge. The acquisition layer was same as described for the comparative examples.

The acquisition layer was glued with glue spirals of Hot melt adhesive/PA—Bostik (H2031F) with Basis weight of 5 gsm onto the nonwoven core cover. The area covered with glue spirals was 65 mm wide, 233 mm long and started 33 mm from absorbent core front edge.

The storage core with acquisition layer made as described above was used to replace the storage core and acquisition patch in a Pampers Baby Dry size 4 diaper commercially available in Germany in April 2012, compacted as described for the comparative examples and analyzed.

Experimental Results

The prototype diapers as indicated above were tested according to the Run-off Test Method indicated above. The results were as follows, with the standard deviation indicated in brackets:

| Option | Comparative Example 1 | Comparative Example 2 | Invention Example |
| --- | --- | --- | --- |
| Gush 1 Run-off, g | 1.9 (1.1) | 4.1 (3.5) | 0.3 (0.1) |
| Gush 2 Run-off, g | 6.2 (4.3) | 8.2 (9.5) | 0.1 (0.1) |
| Gush 3 Run-off, g | 31.4 (9.9) | 25.7 (12.3) | 0.9 (1.5) |
| Gush 4 Run-off, g | 34.4 (4.7) | 29.2 (7.0) | 3.6 (6.4) |
| Total Run-off, g | 73.8 (13.4) | 67.3 (31.0) | 4.8 (8.1) |

The Invention Example has a significantly reduced run-off versus both Comparative Examples.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core for an absorbent article, the absorbent core comprising:
   a first absorbent layer comprising a first substrate, and a layer of cross-linked cellulose fibers deposited on the first substrate; and
   a second absorbent layer comprising a second substrate, a layer of superabsorbent polymer particles deposited on the second substrate, and a fibrous layer of thermoplastic adhesive material covering the layer of superabsorbent polymer particles;
   wherein the first and second absorbent layers are combined together such that at least a portion of the fibrous layer of thermoplastic adhesive material directly contacts at least a portion of the layer of cross-linked cellulose fibers.

2. The absorbent core according to claim 1, wherein the cross-linked cellulosic fibers are chemically cross-linked using a cross-linking agent selected from the group consisting of polycarboxylic cross-linking agents, polyacrylic acids, and mixtures thereof.

3. The absorbent core according to claim 2, wherein the cross-linked cellulosic fibers have between 0.5 mole % and 10.0 mole % of a C[2] to C[9] polycarboxylic cross-linking agent, based on glucose unit.

4. The absorbent core according to claim 1, wherein the layer of cross-linked cellulosic fibers has a water retention value of 25 to 60.

5. The absorbent core according to claim 1, wherein the weight ratio of the superabsorbent polymer particles to the cross-linked cellulose fibers ranges from 1:1 to 10:1.

6. The absorbent core according to claim 1, comprising from 30 to 90 weight percent of the superabsorbent polymer particles by total weight of the core.

7. The absorbent core according to claim 1, comprising from 5 to 50 weight percent of the cross-linked cellulose fibers by total weight of the core.

8. The absorbent core according to claim 1, wherein the layer of superabsorbent polymer particles is deposited on the second substrate on a deposition area comprising discrete land areas separated by junction areas substantially free of the superabsorbent polymer particles.

9. The absorbent core according to claim 1, comprising a longitudinal axis, wherein the layer of superabsorbent polymer particles is profiled along the longitudinal axis of the core so that the basis weight of the superabsorbent polymer particles varies along the longitudinal axis.

10. The absorbent core according to claim 1, wherein the first substrate and the second substrate are made of nonwoven laminates comprising layers of spunbond (S) and meltblown (M) fibers.

11. The absorbent core according to claim 1, comprising a first auxiliary adhesive placed between the first substrate and the layer of cross-linked cellulose fibers and/or a second auxiliary adhesive placed between the second substrate and the layer of the superabsorbent polymer particles.

12. The absorbent core according to claim 1, wherein the layer of superabsorbent polymer particles is deposited on a non-rectangular deposition area.

13. The absorbent core according to claim 1, wherein the layer of superabsorbent polymer particles is deposited on a deposition area which is larger than the area on which the layer of cross-linked cellulose fibers is deposited.

14. The absorbent core according to claim 1, wherein the first substrate or the second substrate is C-wrapped along the longitudinal edges of the core and the other substrate is placed inwardly of these C-flaps.

15. The absorbent core according to claim 1, wherein the first substrate has a surface tension of at least 55 mN/m when being wetted with a saline solution.

16. A method for making an absorbent core comprising the steps of:
   forming a first absorbent layer by depositing a layer of cross-linked cellulose fibers on a first substrate;
   depositing superabsorbent polymer particles on a second substrate;
   forming a second absorbent layer by applying a thermoplastic adhesive material in fibrous form on the superabsorbent polymer particles to form a fibrous layer of thermoplastic adhesive material covering the superabsorbent polymer particles; and
   combining together the first absorbent layer and the second absorbent layer so that at least a portion of the fibrous layer of thermoplastic adhesive material of the second absorbent layer directly contacts at least a portion of the cross-linked cellulose fibers of the first absorbent layer.

17. An absorbent article comprising a topsheet, a backsheet, and an absorbent core disposed between the topsheet and the backsheet, wherein the absorbent core comprises:
   a first absorbent layer comprising a first substrate and a layer of cross-linked cellulose fibers deposited on the first substrate; and
   a second absorbent layer comprising a second substrate, a layer of superabsorbent polymer particles deposited on the second substrate, and a fibrous layer of thermoplastic adhesive material covering the layer of superabsorbent polymer particles;
   wherein the first and second absorbent layers are combined together such that at least a portion of the fibrous layer of thermoplastic adhesive material directly contacts at least a portion of the layer of cross-linked cellulose fibers.

18. The absorbent article according to claim 17, wherein the first absorbent layer is placed closer to the topsheet than the second absorbent layer.

19. The absorbent article according to claim 17, comprising an acquisition layer between the absorbent core and the topsheet.

20. The absorbent article according to claim 19, wherein the acquisition layer is any of shorter, narrower, and partially or completely offset relative to the layer of cross-linked cellulosic fibers.

* * * * *